United States Patent
Lo

(10) Patent No.: US 9,008,832 B2
(45) Date of Patent: Apr. 14, 2015

(54) DIAMOND SORTING SYSTEM

(75) Inventor: Chung Fai Lo, Hong Kong (HK)

(73) Assignee: Eternity Manufacturing Limited, Hong Kong (HK)

( * ) Notice: Subject to any disclaimer, the term of this patent is extended or adjusted under 35 U.S.C. 154(b) by 81 days.

(21) Appl. No.: 13/497,164

(22) PCT Filed: Sep. 22, 2010

(86) PCT No.: PCT/NZ2010/000189
§ 371 (c)(1),
(2), (4) Date: Mar. 20, 2012

(87) PCT Pub. No.: WO2011/037481
PCT Pub. Date: Mar. 31, 2011

(65) Prior Publication Data
US 2012/0179290 A1    Jul. 12, 2012

(30) Foreign Application Priority Data

Sep. 22, 2009  (NZ) .................................... 579884

(51) Int. Cl.
*G06F 7/00* (2006.01)
*G01N 21/87* (2006.01)
*B07C 5/342* (2006.01)

(52) U.S. Cl.
CPC .............. *G01N 21/87* (2013.01); *B07C 5/3422* (2013.01); *B07C 5/3425* (2013.01)

(58) Field of Classification Search
None
See application file for complete search history.

(56) References Cited

U.S. PATENT DOCUMENTS

| | | | |
|---|---|---|---|
| 4,951,825 A | | 8/1990 | Hawkins et al. |
| 5,193,685 A | * | 3/1993 | Trevithick ...................... 209/3.1 |
| 5,506,682 A | * | 4/1996 | Pryor ............................ 356/623 |
| 6,020,954 A | * | 2/2000 | Aggarwal ....................... 356/30 |
| 6,881,907 B2 | * | 4/2005 | Winkelmolen ............... 177/145 |
| 6,980,283 B1 | | 12/2005 | Aggarwal ....................... 356/30 |

FOREIGN PATENT DOCUMENTS

| | | |
|---|---|---|
| CN | 1383199 A | 12/2002 |
| CN | 2753476 Y | 1/2006 |
| DE | 202004009165 U1 | 11/2004 |
| DE | 10 2004 021 689 A1 | 11/2005 |
| DE | 102004021689 A1 * | 11/2005 |

(Continued)

OTHER PUBLICATIONS

International Search Report dated Dec. 7, 2010 issued in connection with corresponding international patent application No. PCT/NZ2010/000189.

(Continued)

*Primary Examiner* — Yolanda Cumbess
(74) *Attorney, Agent, or Firm* — Ostrolenk Faber LLP

(57) ABSTRACT

A diamond sorting system comprising a diamond source for supplying one or more diamonds to be graded by a vision system having one or more cameras arranged to take one or more images of the diamond, and a processor arranged to receive the image data and execute an algorithm on the data to grade the diamond. The sorting system further comprising a diamond collection unit arranged to receive a graded diamond from the vision system and an electromechanical diamond transporter arranged to transport a diamond to be graded from the diamond source to the vision system, and further arranged to transport a graded diamond from the vision system to the diamond collection unit.

30 Claims, 21 Drawing Sheets

(56) References Cited

FOREIGN PATENT DOCUMENTS

| RU | 2 016 672 C1 | 7/1994 |
|---|---|---|
| SU | 1238817 A1 | 6/1986 |
| WO | WO 01/61316 A1 | 8/2001 |
| WO | WO 2005/052540 A2 | 6/2005 |
| WO | WO 2005052540 A2 * | 6/2005 |
| WO | WO 2006/054154 A1 | 5/2006 |

OTHER PUBLICATIONS

Gran Computer Industries, "Model DC3000 Diamond Colorimeter User Guide Revision 1.5" Oct. 2004, retrieved from the Internet, <URL:http://www.sarin.com/downloads/DC3000_1.10_Users_Guide.pdf>, pp. 28-29.

Chinese Office Action mailed Oct. 22, 2013 in corresponding Chinese Application No. 201080035015.1, along with an English language translation thereof.

Chinese Office Action, dated Apr. 8, 2014, issued in corresponding Chinese Patent Application No. 201080035015.1. English translation. Total 14 pages.

Extended European Search Report mailed Feb. 20, 2014 in corresponding European Patent Application No. 10 81 9094.3.

Chinese Office Action mailed Sep. 2 2014 in corresponding Chinese Application No. 201080035015.1, along with an English language translation of relevant portions thereof.

Russian Office Action mailed Oct. 9, 2014 in corresponding Russian Application No. 2012116155, along with an English language translation of relevant portions thereof.

* cited by examiner

DIAMOND SORTING SYSTEM

CROSS REFERENCE TO RELATED APPLICATIONS

The present application is a 35 U.S.C. §371 National Phase conversion of PCT/NZ2010/000189, filed Sep. 22, 2010, which claims benefit of New Zealand Application No. 579884, filed Sep. 22, 2009, the disclosure of which is incorporated herein by reference. The PCT International Application was published in the English language.

FIELD OF THE INVENTION

The invention generally relates to a diamond sorting system and particularly, although not exclusively, relates to an automated diamond sorting system.

BACKGROUND TO THE INVENTION

Diamonds are natural stones that can be graded according to characteristics such as colour and clarity. The grading of a diamond may be used in determining its value for applications such as jewelry making.

Grading is generally done by trained professionals who view diamonds under ten times magnification. The professionals may grade a diamond by observing its colour, and by looking for blemishes on the diamond's surface and inclusions within the diamond in order to determine its clarity. The professional's eyes may become tired after observing and grading many diamonds in one period of time. Further, a professional's eyes may deteriorate with age. These factors may lead to incorrect grading of the diamonds.

It is an object of the invention to provide an improved diamond sorting system or to at least provide the public with a useful choice.

SUMMARY OF THE INVENTION

In a first aspect the invention broadly consists in a diamond sorting system comprising:
a diamond source for supplying one or more diamonds to be graded,
a vision system arranged to receive a diamond from the diamond source for grading the diamond and having:
  one or more cameras arranged to take one or more images of the diamond, and
  a processor arranged to receive data indicative of the one or more images from the one or more cameras, and to execute an algorithm on the data to grade the diamond, a diamond collection unit arranged to receive a graded diamond from the vision system, and
an electromechanical diamond transporter arranged to transport a diamond to be graded from the diamond source to the vision system, and further arranged to transport a graded diamond from the vision system to the diamond collection unit.

Preferably, the diamond source comprises a diamond feeder arranged to provide diamonds oriented for grading to the diamond transporter. Preferably, the diamond feeder comprises a receptacle for containing therein one or more diamonds to be graded and a vibrating platform extending from said receptacle for transporting one or more diamonds onto and along a platform to a position adjacent the diamond transporter.

Preferably, the diamond transporter comprises a robotic arm moveable between the diamond source and the vision system for transporting a diamond from the diamond source to the vision system for grading. Preferably, the robotic arm comprises a body part rotatable between a pick-up position adjacent the diamond source and a drop position adjacent the vision system. Preferably an arm extends from the body part and comprises a suction head at a distal end thereof, wherein the suction head is arranged to apply a suction force for picking up the diamond from the diamond source when the body part is in the pick-up position and to at least partially remove the suction force when the body part is in the drop position to release the diamond onto the vision system for grading. Preferably the arm is pivotably coupled to the body part to enable the suction head to pivot towards or away from a diamond when the body part is in the pick-up or drop position.

Preferably, the diamond transporter comprises a robotic arm moveable between the vision system and the diamond collection unit for transporting a graded diamond from the vision system to the collection unit. Preferably, the robotic arm comprises a first body part rotatable between a pick-up position adjacent the vision system and a drop position adjacent the collection unit. Preferably an arm extends from the body part and comprises a suction head at a distal end thereof, wherein the suction head is arranged to apply a suction force for picking up a diamond from the vision system when the body part is in the pick-up position and to at least partially remove the suction force when the body part is in the drop position to release the diamond at the collection unit. Preferably the arm is pivotably coupled to the body part to enable the suction head to pivot towards or away from a diamond when the first body part is in the pick-up or drop position. Preferably the robotic arm further comprises a second body part to which the first body part is rotatably coupled, and wherein the second body part is rotatable about a spaced and substantially parallel axis to that of the first body part.

Preferably, the diamond transporter comprises two separate robotic arms.

Preferably, the diamond collection unit is segmented into a plurality of segments, each corresponding to a particular diamond grade. More preferably, the diamond collection unit comprises a segmented platform, each segment corresponding to a particular diamond grade. Preferably the diamond collection unit comprises a segmented platform, each segment having a container for retaining a particular grade of diamond. Preferably the robotic arm moveable between the vision system and the diamond collection unit is moveable over any one of the containers of the collection unit. Preferably the containers are arranged in a matrix.

Preferably the system further comprises a housing for retaining the vision system, the diamond source, the transportation system and the diamond collection unit.

Preferably, the vision system is arranged to grade the diamond by either colour or clarity. More preferably, the vision system is arranged to grade the diamond by both colour and clarity.

Preferably, the vision system comprises at least one camera and an imaging region for retaining a diamond to be imaged by the at least one camera. More preferably, a first camera comprises a lens arranged to capture an image suitable for colour grading of the diamond, and a second camera comprises a lens arranged to capture an image suitable for clarity grading of the diamond. Preferably only one image is required from each of said first and second cameras to grade the diamond.

Preferably, each camera comprises a charged-couple device.

Preferably, the vision system comprises an integration sphere arranged to receive a diamond and to provide a substantially even light distribution around the diamond to be imaged. More preferably, the integration sphere comprises a moveable platform for transporting the diamond into the integration sphere to be imaged and out of the integration sphere to be transported to the collection unit. Preferably the platform is rotatable and passes through a slit in the sphere to move a diamond on the platform into and out of the integration sphere. Preferably the platform is a disk having at least one recessed stage for retaining a diamond. More preferably the disk comprises three recessed stages that are radially spaced such that during imaging, one stage is within the integration sphere, one stage is adjacent the transportation system for receiving a diamond from the diamond source and one stage is adjacent the transportation system for providing a graded diamond to be delivered to the collection unit.

Preferably, the vision system comprises a light source arranged to light the diamond to be imaged.

Preferably, the vision system comprises one or more optic fibres arranged to transport light from the light source to the integration sphere.

Preferably the system further comprises a housing for retaining the vision system, the diamond source, the transportation system and the data collection unit.

Preferably the system further comprises a dust ionizer in the housing for neutralizing static charge within the housing.

In a second aspect the invention broadly consists in an automated method of sorting a diamond comprising the steps of:

transporting a diamond from a diamond source to a vision system;

taking one or more images of the diamond;

processing data indicative of the images to grade the diamond;

transporting the diamond to a segment of a diamond collection unit corresponding to the grade of the diamond so that the diamond is sorted in the diamond collection unit according to its grade.

Preferably, the diamond is graded by its colour. More preferably, the saturation value of the image of the diamond is extracted in order to grade the colour of the diamond.

Preferably, the diamond is graded by its clarity. More preferably, large intensity changes in the image of the diamond are identified in order to grade the clarity of the diamond.

In a third aspect the invention broadly consists in a method of grading a diamond comprising the steps of:

taking one or more images of the diamond; and processing data indicative of the images to grade the diamond.

Preferably, the diamond is graded by its colour. More preferably, the saturation value of the image of the diamond is extracted in order to grade the colour of the diamond.

Preferably, the diamond is graded by its clarity. More preferably, large intensity changes in the image of the diamond are identified in order to grade the clarity of the diamond.

The term "comprising" as used in this specification and claims means "consisting at least in part of". When interpreting each statement in this specification that includes the term "comprising", features other than that or those prefaced by the term may also be present. Related terms such as "comprise" and "comprises" are to be interpreted in the same manner.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIGS. 1b, c and d are plan, front and side views of the diamond sorting system of FIG. 1a;

DETAILED DESCRIPTION OF PREFERRED EMBODIMENTS

Figure 1A:
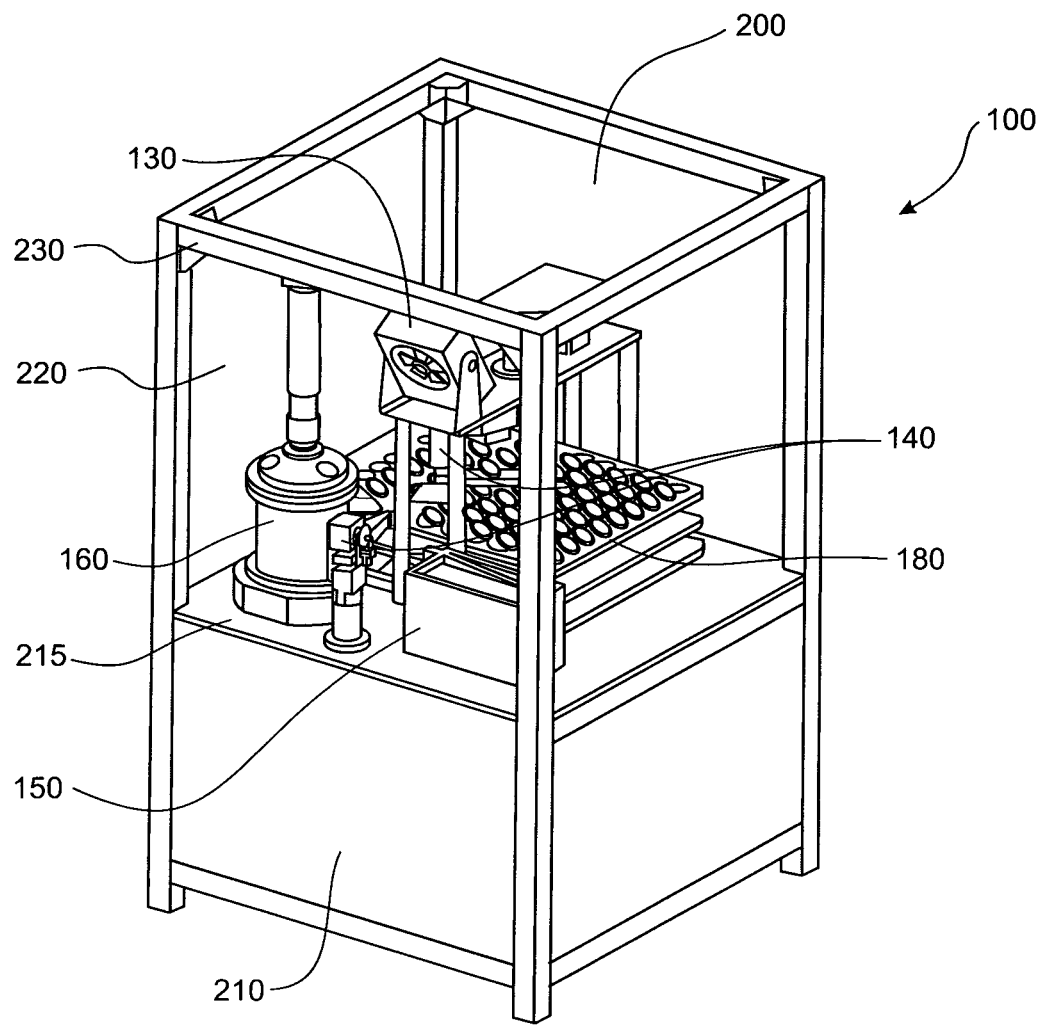
FIG. 1a is a perspective view of a preferred embodiment diamond sorting system of the invention.
Figure 1D:
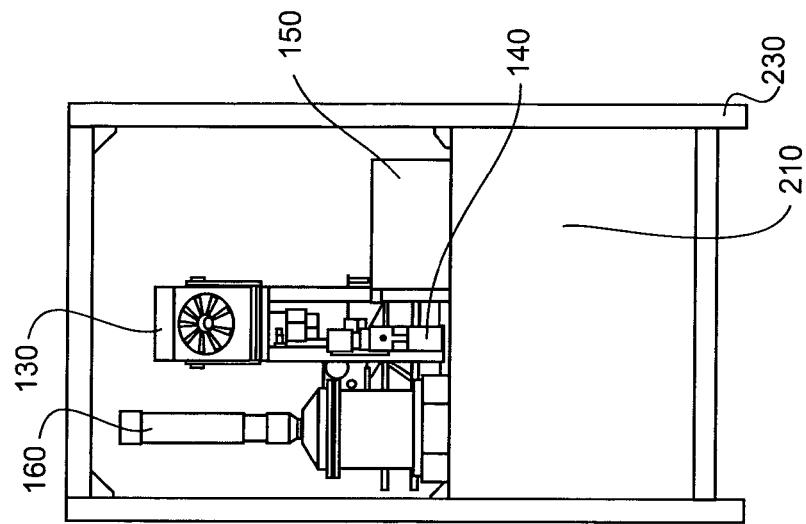
Figure 1C:
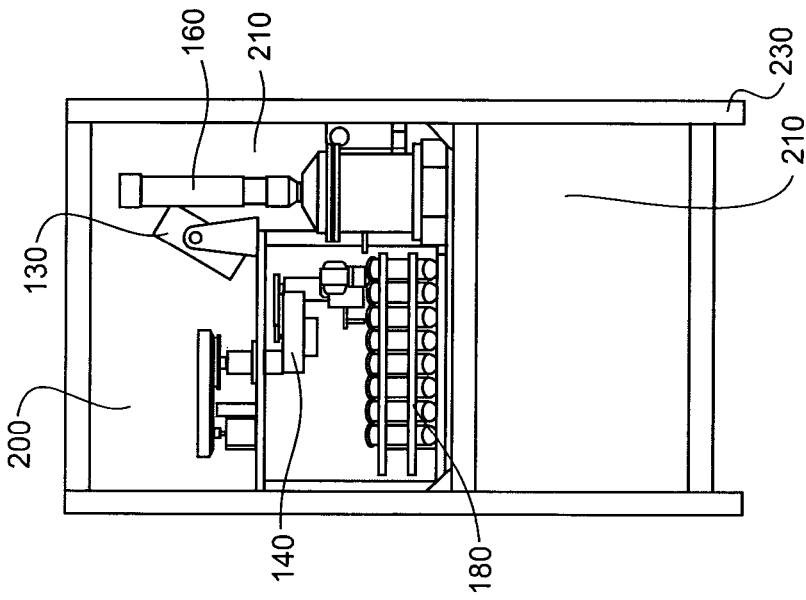
Figure 1B:
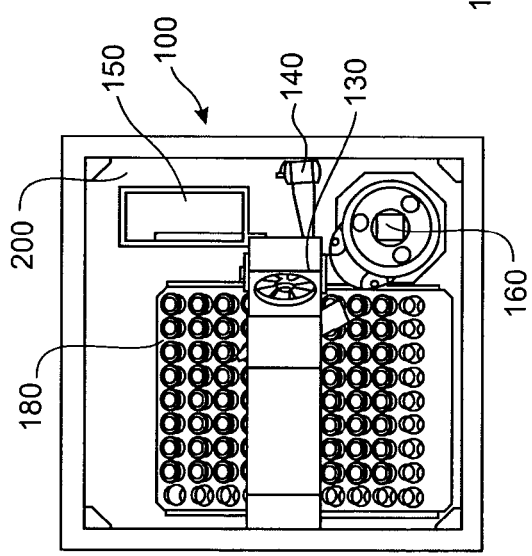

The invention generally relates to an automated diamond sorting system that can sort diamonds into different grades through an electromechanical diamond moving system, and an image processing based vision system.

Referring to FIGS. 1a-1d, a diamond sorting system 100 may be used to grade diamonds through an automated process. The diamond sorting system 100 comprises an electromechanical system 140 for transporting diamonds within the system. The diamond sorting system 100 also comprises a vision system 160 for grading each diamond according to certain characteristics of that diamond. The diamonds may each be graded by their colour, clarity, or both, or any other suitable characteristic. Generally, the electromechanical system 140 transports a diamond from a diamond source 150 to the vision system 160 for grading. Once graded, the electromechanical system 140 then transports the diamond from the vision system 160 to a diamond collection unit 180.

The diamond sorting system 100 may be provided in a housing or casing 200. The casing may house the system's processor or computer and actuators such as motors in a lower part 210 made from metal, wood, plastic or any other suitable material. The lower part may also provide a platform 215 for supporting the system components 130, 140, 150, 160 and 180. The casing may also comprise an upper glass section 220 so that the system components may be observed while it is in use. A frame 230 made from any suitable material may be used to support the upper 220 and lower 210 sections.

In the preferred embodiment shown, the diamond sorting system 100 is housed within a structure that is 910 mm high by 560 mm wide by 560 mm deep. It will be appreciated that the system may be housed within other sized structures depending on the complexity of the system and the sizes of the components used.

Figure 2:
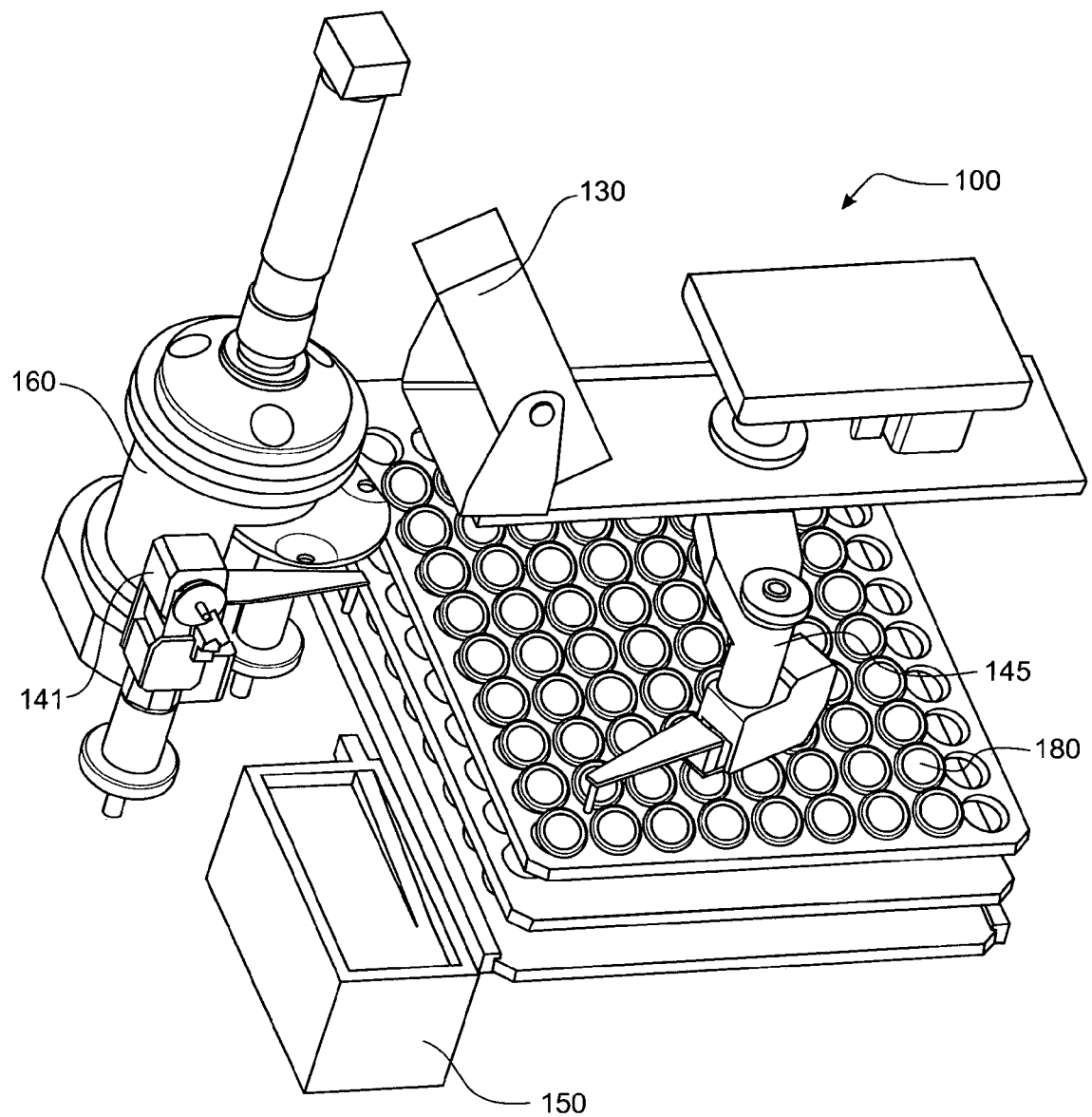
FIG. 2 is a more detailed perspective view of the diamond sorting system of FIG. 1a without the housing.

Referring to FIG. 2, the system 100 is shown without the housing 200. The electromechanical system 140 comprises two robotic arms 141 and 145. The first robotic arm 141 is moveable between a diamond source 150 and the diamond vision system 160 to deliver diamonds from the source 150 to the vision system 160 to be sorted. The second robotic arm 145 is moveable between the vision system 160 and a diamond collection unit 180 where the graded diamonds are collected and grouped according to their grade. A dust ionizer 130 may be provided in the housing 200 for neutralizing static charge within the housing 200.

Electromechanical System and Diamond Collection Unit

The electromechanical system 140 comprises a diamond transporter arranged to transport a diamond from a diamond source 150 to the vision system 160 for grading. The diamond transporter is also arranged to transport the diamond from the vision system 160 to the diamond collection unit 180 once graded. The diamond transporter may comprise one single device arranged to transport the diamond around all areas of the system. Alternatively, the diamond transporter may comprise two or more devices, where each device may be arranged to transport the diamond around specific areas of the system. The diamond transporter may comprise one or more robotic arms or any other suitable mechanism or device arranged to move the diamonds.

In the preferred form diamond sorting system shown, the diamond transporter comprises a first robotic arm 141 arranged to transport a diamond from the diamond source 150 to the vision system 160. The diamond transporter also comprises a second robotic arm 145 arranged to transport a graded diamond from the vision system 160 to a diamond collection unit 186. Other embodiment diamond sorting systems may comprise only one robotic arm arranged to move the diamond from the diamond source 150 to the vision system 160 and then to the diamond collection unit 180.

Figure 3A:
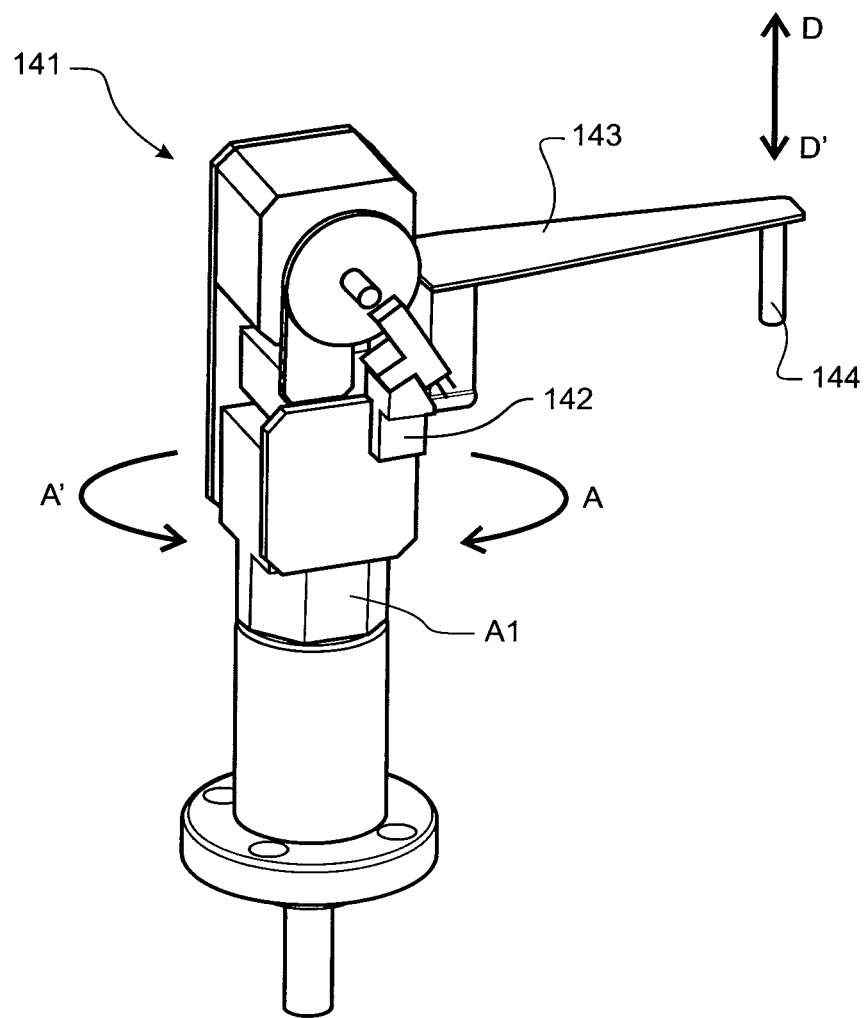
FIG. 3a is a perspective view of a first robotic arm of the transportation system of the diamond sorting system of FIG. 2.
Figure 3B:
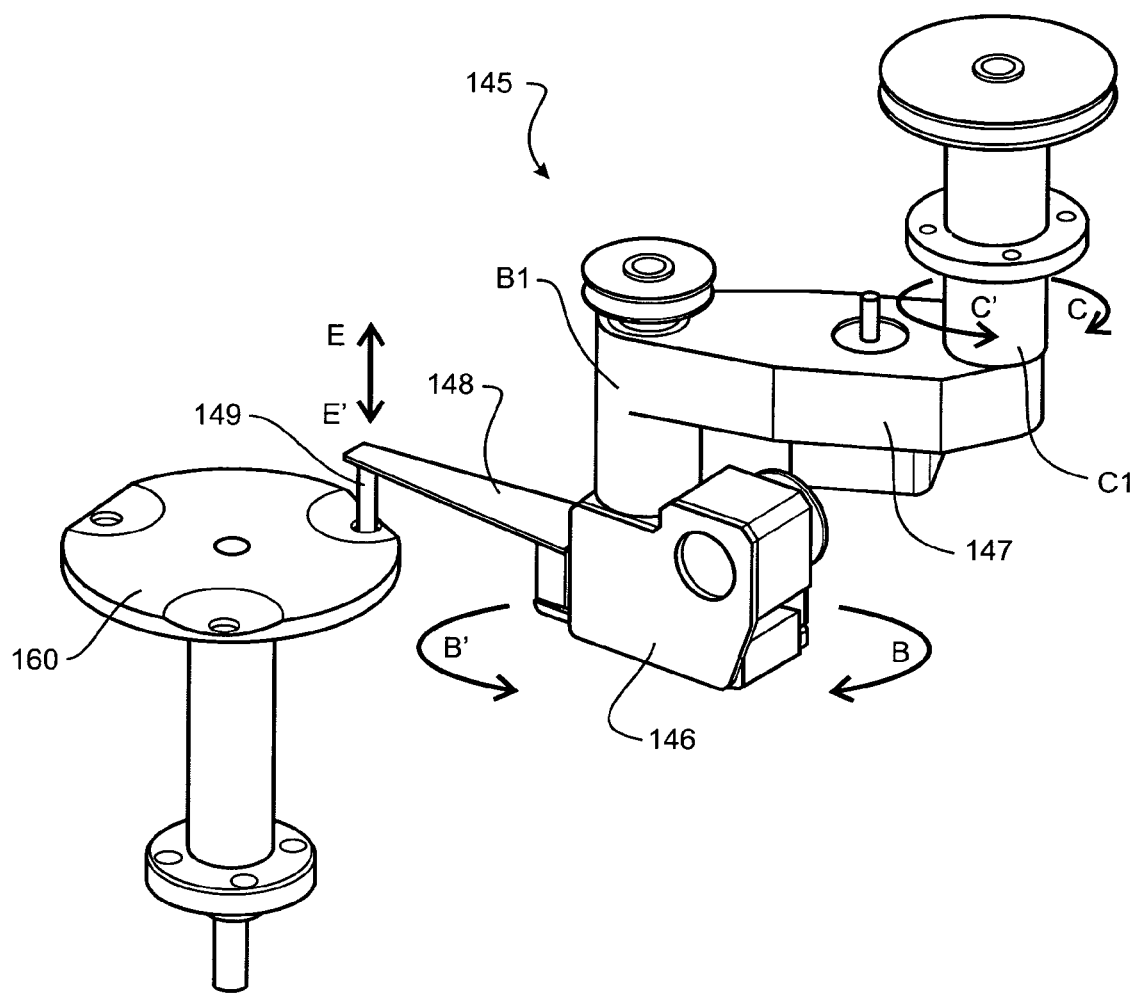
FIG. 3b is a perspective view of a second robotic arm of the transportation system of the diamond sorting system of FIG. 2.

Referring to FIGS. 3a and 3b, the first robotic arm 141 comprises a body part 142 that is rotatable clockwise and anti-clockwise as indicated by arrows AA'. The second robotic arm 145 comprises lower and upper body parts 146 and 147 that are also rotatable clockwise and anti-clockwise as indicated by arrows BB' and CC' respectively. Rotation of the body parts 142, 146 and/or 147 may be actuated by an electric motor controlled by a computer of the diamond sorting system 100 for example. The first robotic arm 141 may also comprise an arm component 143 that is pivotably coupled at its proximal end to the body part 142. The second robotic arm 145 may also comprise an arm component 148 that is pivotably coupled at its proximal end to the lower body part 146. The arms 143 and 148 may each pivot up and down about a pivot axis as indicated by arrows DD' and EE'. The pivot axes of the arms 143 and 148 are preferably substantially perpendicular to the rotation axes of body parts 142 and 146/147 respectively. Pivotal movement of the arms 143 and/or 148 may be actuated by an electric motor controlled by a computer of the diamond sorting system 100 for example. The computer controlling the electric motors mentioned above may be housed within the lower part 210 of the housing 200 of FIG. 1a or any other suitable place. In particular the first robotic arm 141 comprises a single articulated joint A1 to which body 142 is coupled; allowing free circular motion of the body 142 in the clockwise and anticlockwise directions. Arm component 143 extends transversely from and is pivotably coupled to the body part 142 to achieve up and down movement DD' of the arm 143 for picking up and placing of diamonds. The transportation system 140 is designed such that the degree of rotation of body part 142 and the length of arm 143 are suitable to enable at least the distal end of the arm 143 to reach both the diamond source 150 and the vision system 160. A vacuum suction head 144 at a distal end of the arm 143 is provided to pick a diamond up from the source 150 and place it on the vision system 160.

The second robotic arm 145 comprises two articulated joints B1 and C1. These joints allow free circular motion of body parts 146 and 147 respectively in both clockwise and anticlockwise directions. Body parts 146 and 147 are linked at joint B1 and their axes of rotation are spaced but parallel to one another. This allows the arm 148 to extend into any X-Y coordinate within its working envelope to reach confined areas and retract or "fold up" out of the way from the rest of the system 100. Also, with the aid of the Z axis vacuum suction head 149 at the distal end of arm 148, up and down motion for picking and placing of diamonds is achieved. This is advantageous for transferring graded diamonds 10 from the vision system 160 to the collection unit 180.

Figure 4:
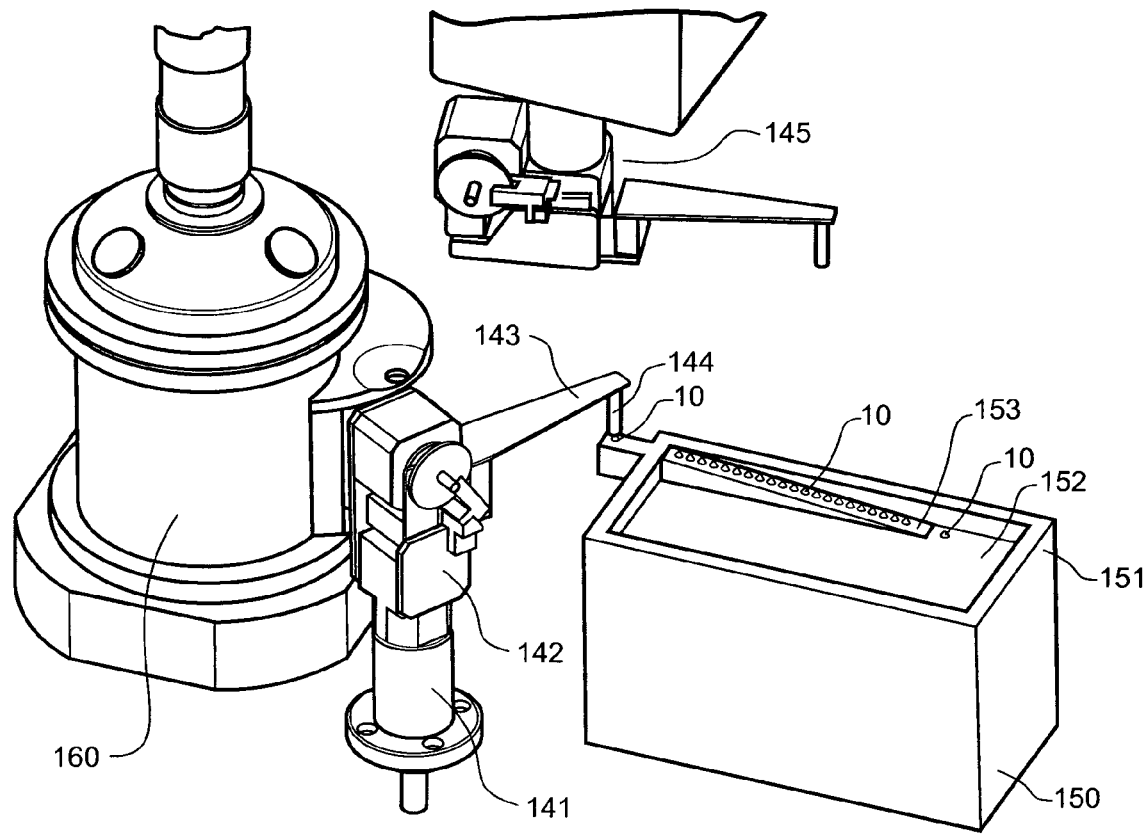
FIG. 4 is a perspective view of the first robotic arm collecting a diamond from a diamond feeder of the diamond sorting system.
Figure 5:
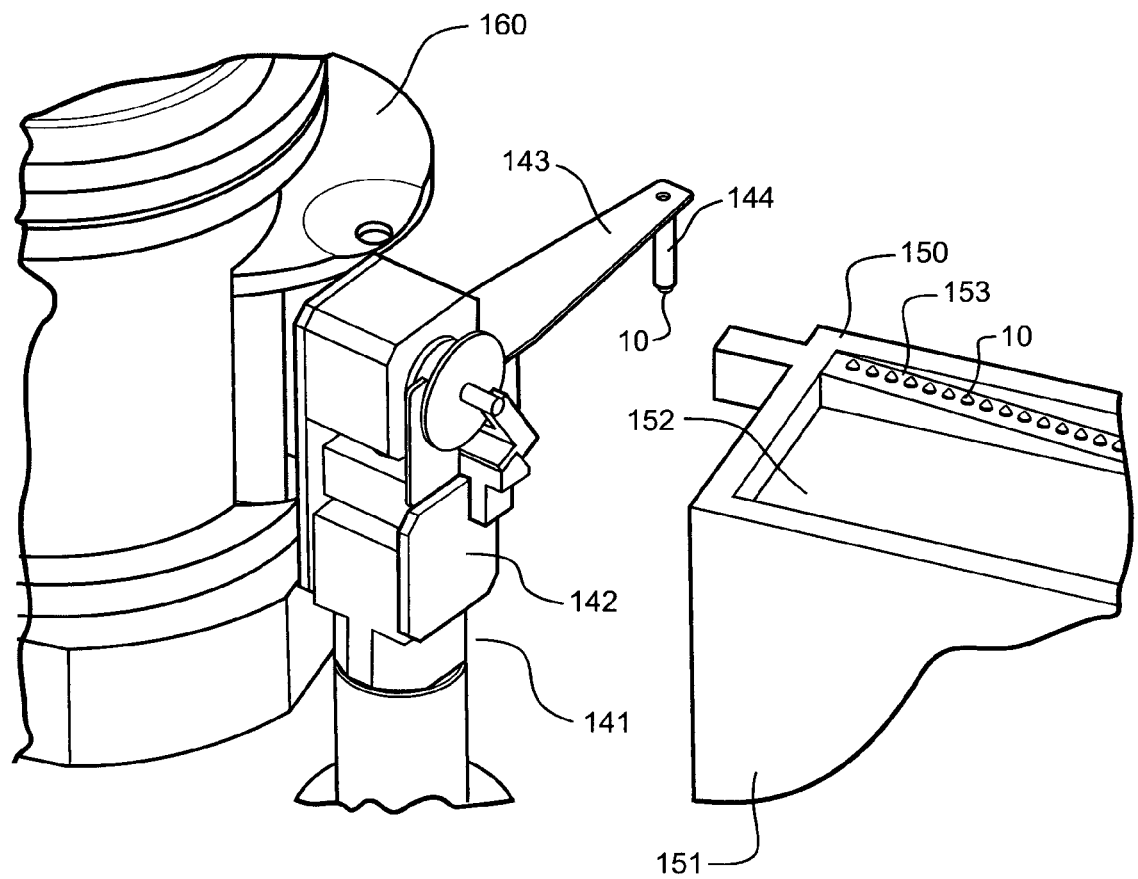
FIG. 5 is a close up perspective view of the first robotic arm transporting the diamond of FIG. 4 to a vision system of the diamond sorting system.
Figure 6:
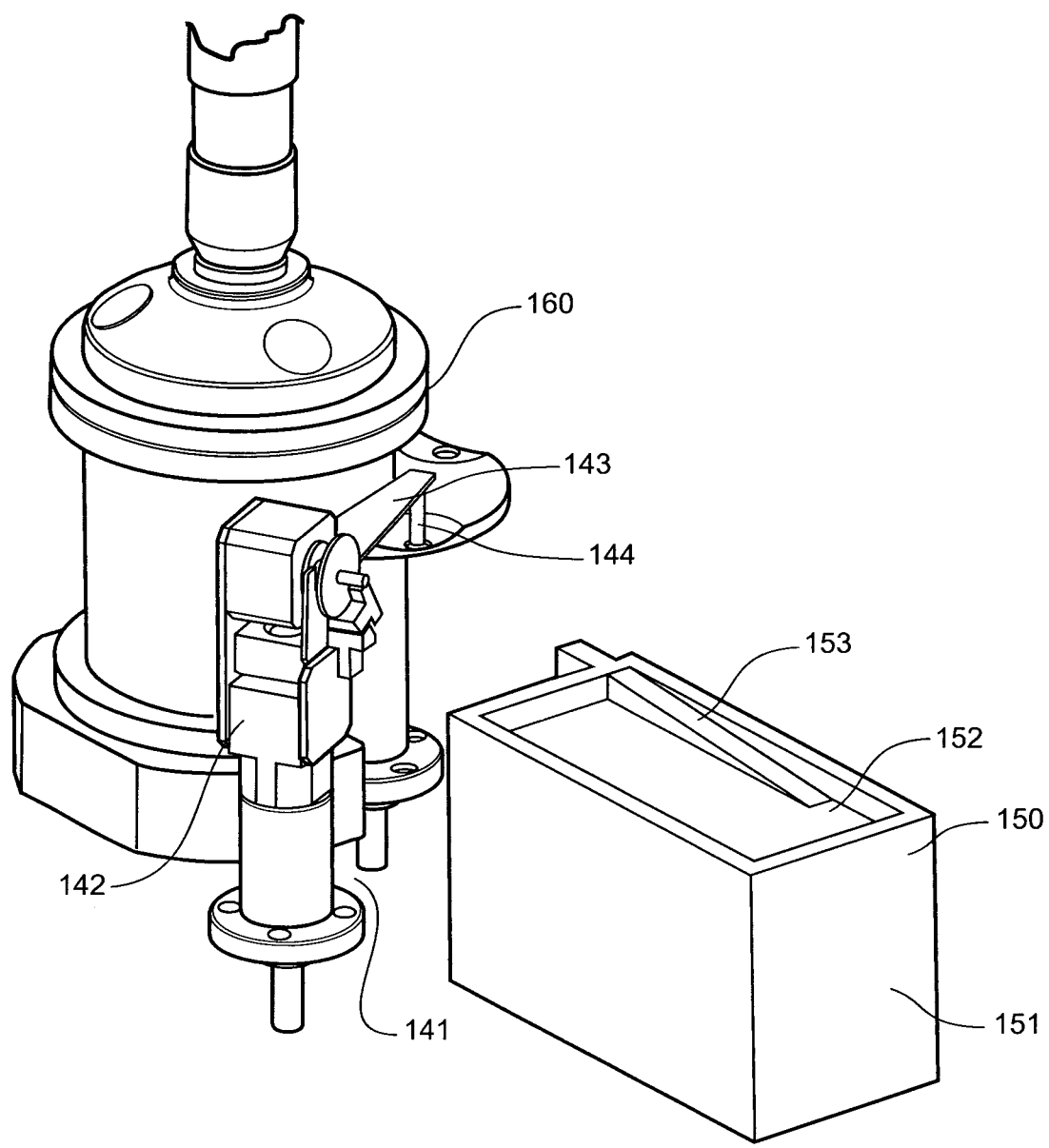
FIG. 6 is a perspective view of the first robotic arm dropping the diamond of FIG. 5 off at the vision system.

As shown in FIGS. 4, 5 and 6, the first robotic arm 141 may be controlled to move its suction head 144 into contact with a diamond 10 waiting at the diamond source 150. A suction force may then be applied by the suction head 144 to the diamond 10 so that it may be picked up by the first robotic arm 141 and moved to the vision system 160. The suction force may then be removed from the diamond 10 to drop it.

Figure 7:
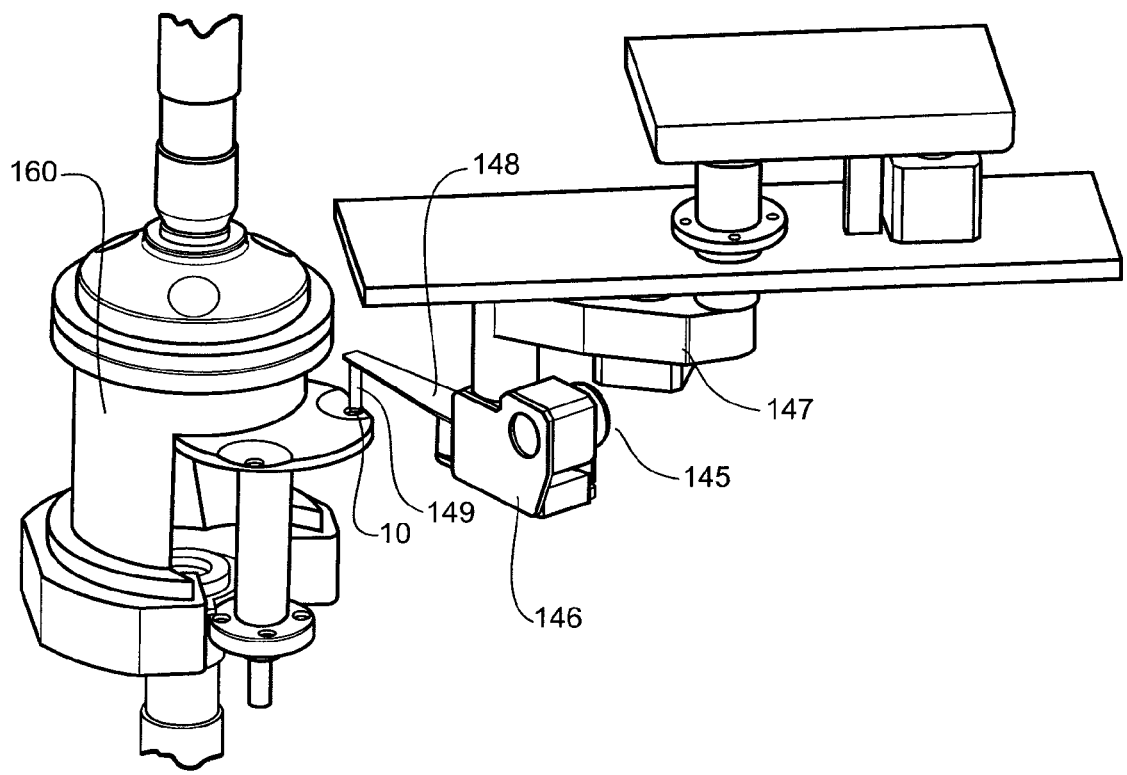
FIG. 7 is a perspective view of a second robotic arm of the transportation system collecting a graded diamond from the vision system.
Figure 8:
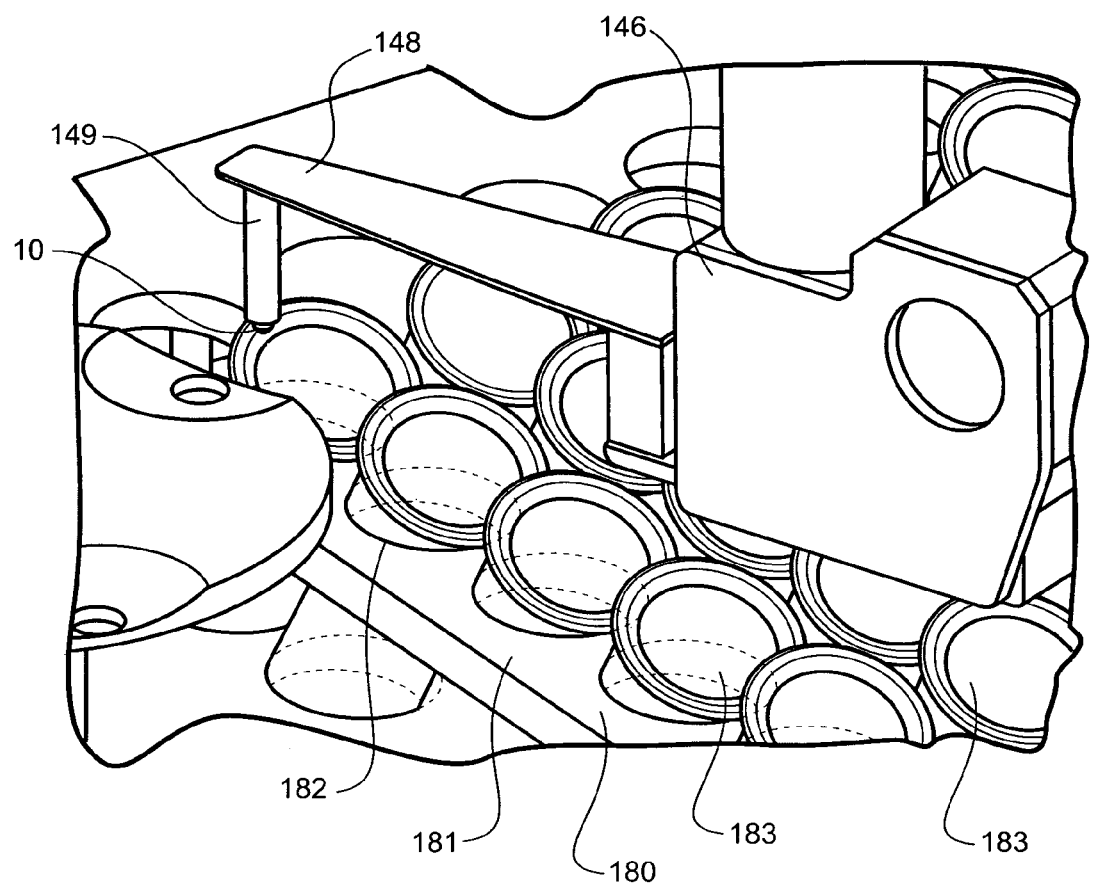
FIG. 8 is a close-up perspective view of the second robotic arm transporting the diamond of FIG. 7 to a diamond collection unit of the diamond sorting system.
Figure 9:
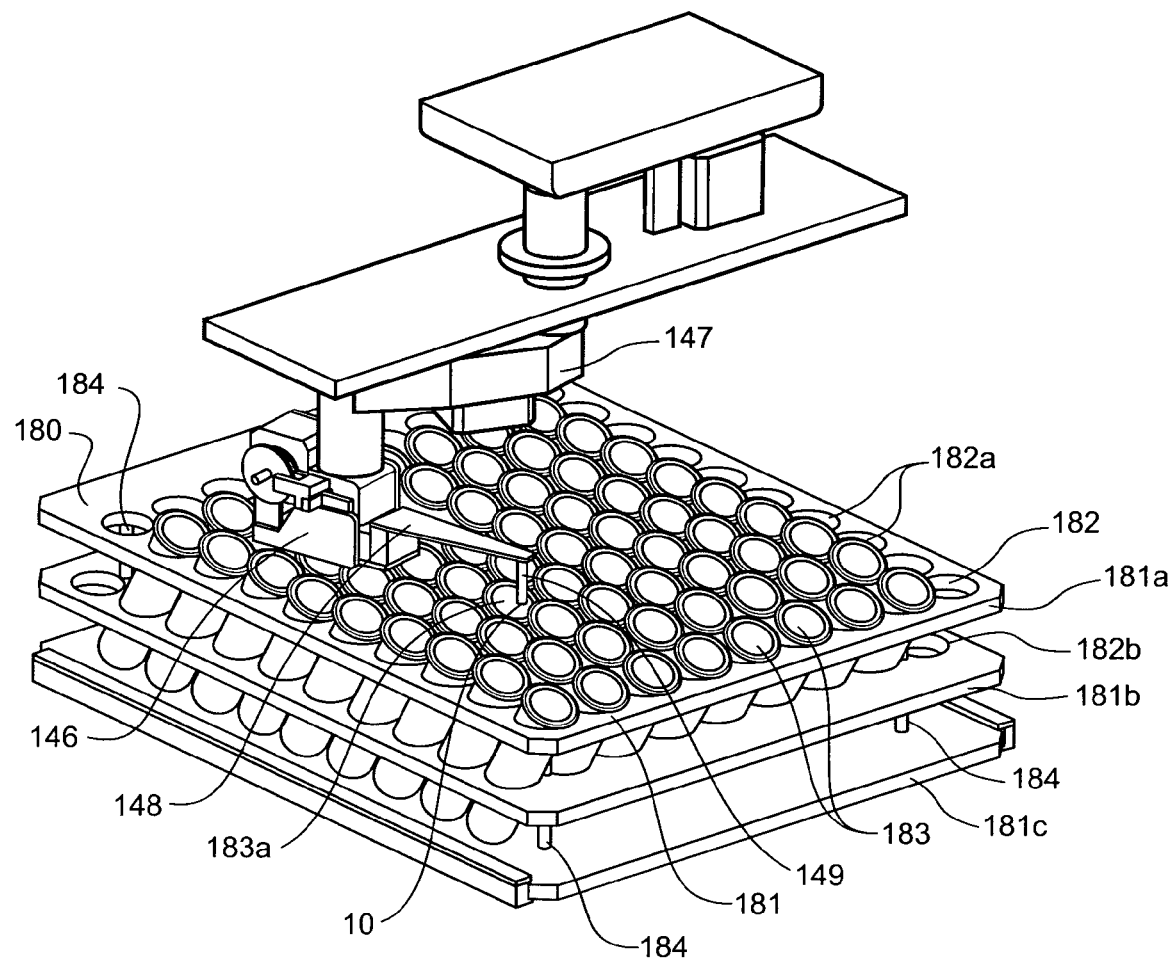
FIG. 9 is a perspective view of the second robotic arm of FIG. 8 dropping the graded diamond off at the appropriate bin of the collection unit.

Referring to FIGS. 7, 8 and 9 similarly, the second robotic arm 145 may be controlled to move its suction head 149 into contact with a graded diamond 10 waiting at the output of the vision system 160. A suction force may then be applied by the suction head 149 to the diamond 10 so that it may be picked up by the second robotic arm 145 and moved to the diamond collection unit 180. The suction force may then be removed from the diamond 10 to drop it into the appropriate place 183a at the collection unit 180.

The suction heads 144/149 may be made from plastic, rubber, or any other suitable material. The diamond sorting system 100 may comprise a pneumatic system connected to the suction heads 144/149 by hoses for example so that the suction heads 144/149 may be able to generate a sucking force. The pneumatic system may be controlled by the computer. Any method other than suction force suitable for picking up, transporting and placing a diamond may be used. In this specification the terms drop or dropping are intended to also cover situations where the diamond is released or placed gently on a surface and not necessarily released from a height.

Referring back to FIGS. 4 and 5, in the preferred embodiment the diamond source 150 comprises a diamond feeder 151 arranged to provide diamonds 10 to the first robotic arm 141 in a known position and orientation. The diamond feeder 151 may comprise a receptacle 152 for holding a plurality of diamonds 10 to be graded. Generally, the diamonds 10 held in the receptacle 152 are provided in a disoriented fashion (not shown). The diamond feeder 151 may comprise a vibrating track 153 which vibrates to orient the diamonds 10 and to facilitate transportation of the diamonds along the length of the track. The diamond feeder 151 may vibrate so that one or more diamonds 10 are vibrated from the receptacle 152 onto the bottom of the vibrating track 153. The diamond is then vibrated along the length of the vibrating track 153 until it reaches the end at the top of the receptacle wall ready for pick-up by the robotic arm 141. The diamond 10 is oriented into a known position during its movement along the track. For example, diamonds that are cut so that one end is larger or heavier than the other end (a brilliant cut) may end up sitting on the smaller, lighter end by the time they have been vibrated along the length of the track 153. The diamond 10 may be lying on its side in the receptacle 152 initially. By the time the diamond has been vibrated along the vibrating track 153 the diamond may have changed orientation so that it is sitting on its table. Generally, if a plurality of diamonds are vibrated along the vibrating track 153, they will all end up in the same orientation by the end of the track 153 so that they are ready to be picked up by the first robotic arm 141 for transportation to the vision system 160.

Figure 10:
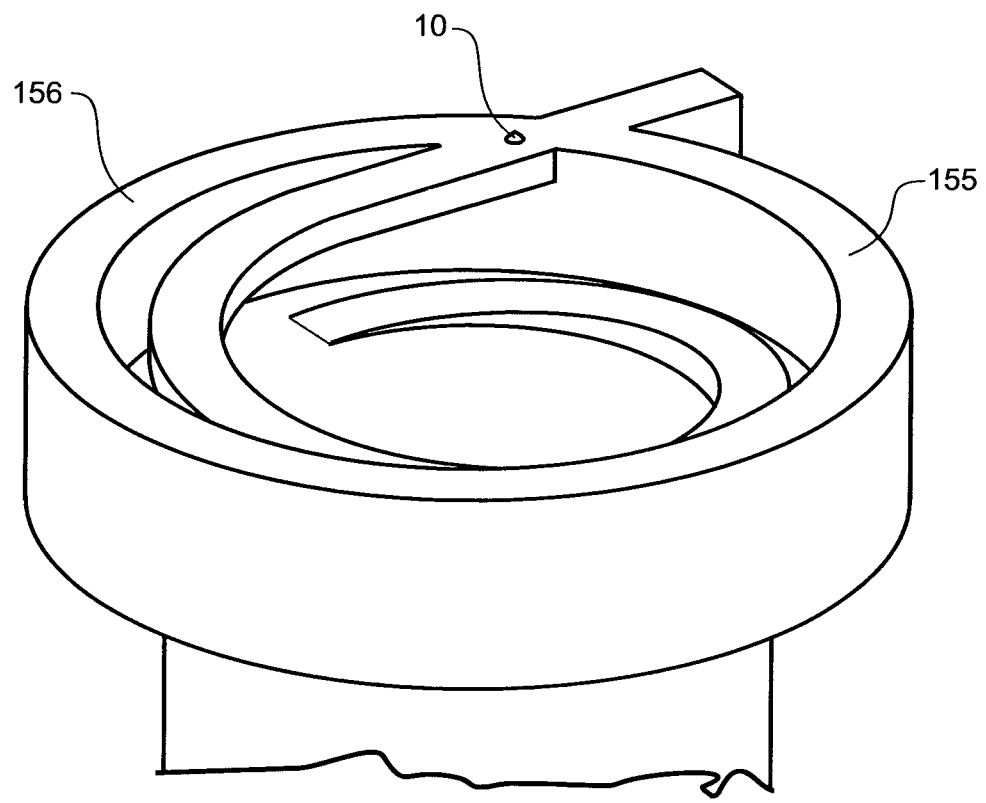
FIG. 10 is a perspective view of an alternative form diamond feeder of the diamond sorting system.

The feeder and receptacle may not necessarily be in the form shown and can take on any shape such as a bowl 155 as shown in FIG. 10. The vibrating track may also take on a different shape such as the spiral 156 shown looped around the bowl 155. Any suitable length of track may be employed as required by the system 100.

A hopper or any other suitable diamond source 150 that orients the diamonds 10 into an orientation suitable for grading may be used instead.

Referring to FIGS. 4, 5 and 6, in transporting a diamond 10 from the diamond feeder 151 to the input of the vision system 160, the body 142 of the first robotic arm 141 may rotate towards the top of the vibrating track 153. The arm 143 may then pivot so that the suction head 144 contacts the diamond 10 at the top of the vibrating track 153 (FIG. 4). Suction may then be applied to the diamond 10 and the arm 143 may then be pivoted in the opposite direction to pick the diamond 10 up. The body 142 may then rotate the arm 143 holding the diamond 10 towards the input of the vision system 160 (FIG. 5). Once it is adjacent to the input of the vision system 160, the arm 143 may then be pivoted towards the input of the vision system 160 to place the diamond 10 in the appropriate place (FIG. 6). Suction may be removed so that the diamond 10 is left in a known orientation at the input of the vision system 160. The body 142 and arm 143 may then rotate away from the vision system 160 and await instructions to pick up the next diamond from the feeder 151.

Referring to FIGS. 8 and 9, the diamond collection unit 15 comprises a segmented platform 181 having a container 183 at each segment for retaining a particular grade of diamond. In the preferred embodiment, the diamond collection unit 180 comprises a table 181 with a plurality of apertures 182 arranged to receive containers or bins 183 for collecting graded diamonds 10. Each bin 183 may correspond to a particular diamond grade. For example, one bin may correspond to a diamond grading of slightly included clarity and near colourless colour, while another bin may correspond to a diamond grading of slightly included clarity and faint yellow colour, and yet another bin may correspond to a diamond grading of very slightly included clarity and near colourless colour. The number of bins provided should be equal to the number of possible clarity gradings multiplied by the number of possible colour gradings. There may be one bin provided for each combination of possible clarity grading with each possible colour grading. As shown, the apertures 182 and bins 183 may be arranged in a matrix to organise the diamond grading in rows and columns of clarity and colour. The computer may have in memory a database or map indicative of where each bin 183 corresponding to a particular grade of diamond is located on the table 181. Using this information, once a particular diamond 10 has been graded, the computer can fetch the row and column location of the appropriate collection bin 183 and send instructions the robotic arm 145 to move to the appropriate position and place the graded diamond 10 in the bin 183. Repeating this procedure multiple times for multiple diamonds 10 may result in diamonds of the same grading being sorted in the same bin 183. A user can then retrieve the diamonds 10 sorted by their grades.

The second robotic arm 145 is preferably capable of reaching all the bins 183 on the table 181 so that diamonds 10 can be deposited in the appropriate bin 183.

Referring to FIG. 7 also now, in transporting a diamond 10 from the output of the vision system 160 to the diamond collection unit 180 the body parts 146 and 147 of the second robotic arm 145 may rotate towards the vision system 160. Once adjacent to the output of the vision system 160, the arm 148 may then pivot so that the suction head 149 contacts the diamond 10 at the output of the vision system 160 (FIG. 7). Suction may then be applied to the diamond 10 and the arm 148 may then be pivoted in the opposite direction to pick the diamond 10 up (FIG. 8). The body parts 146 and 147 may then rotate towards the diamond collection unit 180 so that the diamond 10 is aligned with and suspended over the appropriate bin 183 of the diamond collection unit 180 (FIG. 9). Suction may be removed so that the diamond 10 falls into the appropriate bin 183*a*.

In the preferred embodiment, the second robotic arm 145 comprises of two body parts 146 and 147 that are each rotatable about parallel but spaced axes. This provides an arrangement that allows the arm 148 (and in particular the end of the arm 148 where the suction head 149 extends) to be moved across all areas of the table 181 carrying collection bins 183.

In addition or in an alternative embodiment, the table 181 is also moveable or rotatable such that it can move appropriately before, during or after movement of the robotic arm 145 to aid in alignment of the suspended diamond 10 over the appropriate bin 183.

Referring to FIG. 9, the table 181 may compose a number of stacked trays 181*a-c* for containing bins 183 therein. Trays 181*a* and 181*b* may contain an identical but misaligned set of apertures 182*a* and 182*b* respectively for diagonally receiving each bin 183 through a pair of misaligned apertures as shown. This allows each bin to rest against the periphery of its corresponding apertures 182*a*/182*b*. A base tray 181*c* is provided for supporting the bottom of each bin 183. Pins 184 extend between the trays 181*a-c* to separate, couple and align the trays 181*a*-*c* with one another. Any other suitable method or arrangement for collecting the graded diamonds 10 may be used.

Generally, 0.8 mm to 3 mm diamonds may be graded by the diamond sorting system 100. However, diamonds of any suitable size may be graded. The robotic arms 141, 145 and the vision system 160 may be controlled with precision or accuracy down to 0.08 mm for systems that are arranged to grade 0.8 mm to 3 mm diamonds.

It should be noted that the diamond may be transported from the diamond source 150 to the vision system 160, and from the vision system 160 once graded to the diamond collection unit 180 in any suitable manner without departing from the spirit and scope of the invention.

All moving parts or mechanical devices of the electromechanical system 140 may be actuated in any suitable manner. For example, electric motors may actuate movement of the robotic arms 141 and 145, of any moving parts in system 160 as described further below and of the table 181 if moveable/rotatable. An electric motor with an asymmetrical weight associated with the diamond feeder 151 may actuate vibrations in the diamond feeder 151. The actuators may be controlled by one or more computers or processors associated with the diamond sorting system 100. Alternatively or in addition a hydraulic system may be employed in connection with any of the moving parts.

Dust Ionizer

Referring back to FIG. 2, in the preferred embodiment a dust ionizer 130 is provided for neutralizing static charge within the housing 200. In the preferred form the dust ionizer 130 operates constantly once the machine/system 100 is turned on. The ionizer 130 generates a flow of positive and negative ions leading to an exchange of electrons with dust and an anti-aliasing filter, giving the dust particles a neutral charge. With no more electrostatic charge, the particles will stop sticking to each other so that all the dust can easily be removed from the system 100. This insures a clean and clear diamond surface for color and clarity grading.

The dust ionizer 130 also aids in eliminating the electrostatic charge inside the track 153 of the vibration feeder 151 during operation. Without electrostatic charge, diamonds will stop sticking on top of the track 153 of the feeder 151. This insures a stable supply of diamonds during the automation process.

A dust ionizer 130 may not necessarily be employed in the system 100. However, it is a preferable feature as it helps measure static electricity, ionize static charge, continuously monitor dust particles and protect the production area from dust particles in factory processing and test environments.

Vision System

Figure 11:
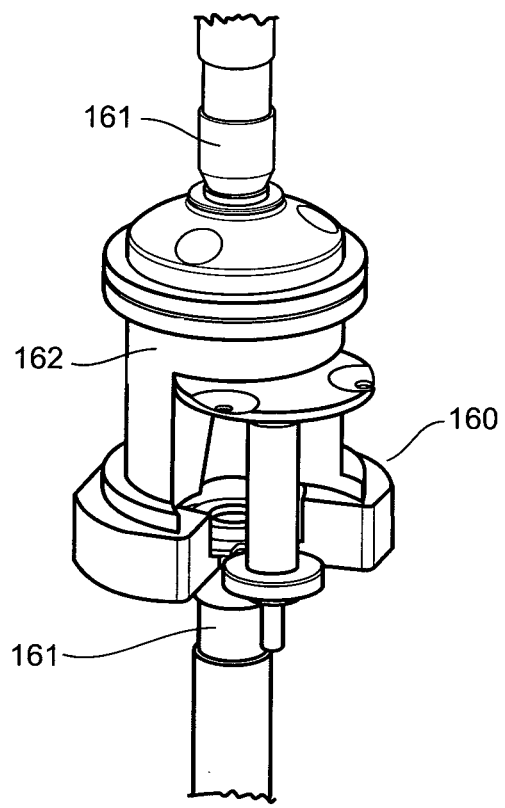
FIG. 11 is a perspective view of the exterior of a vision system of the preferred form diamond sorting system.
Figure 12:
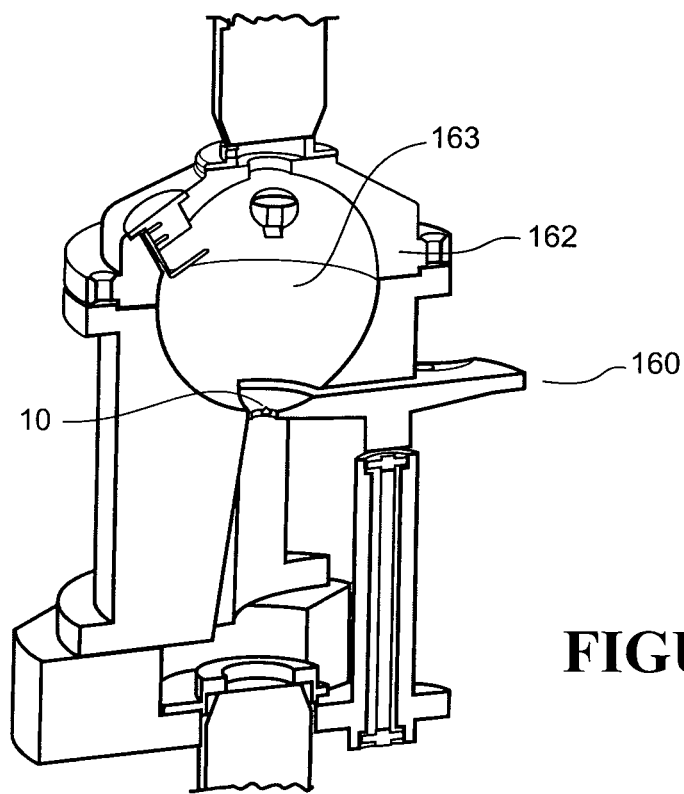
FIG. 12 is a cutaway perspective view showing the interior of the vision system of FIG. 11.

Referring to FIGS. 11 and 12, the vision system 160 is arranged to receive a diamond 10 from the diamond source 150 via the electromechanical system 140. The vision system 160 comprises one or more cameras (not shown) arranged to take one or more images of the diamonds 10. The images or data indicative of the images taken by the camera may be processed by an image processing system in order to grade the diamond 10. Preferably, the vision system 160 comprises two cameras located on either side of the vision system 160. One camera is arranged to capture images for grading the colour of a diamond 10 and the other camera is arranged to capture images for grading the clarity of a diamond 10. Each camera may have a corresponding lens 161 arranged to assist in capturing information related to either colour or clarity of the diamonds 10. Preferably, the cameras are digital and may comprise a CCD chip, a CMOS chip, or any Other suitable device. Alternatively, the diamond sorting system 100 may comprise three or any other suitable number of cameras.

The diamond 10 may be placed inside an integration sphere 162 for capturing of the images. The integration sphere may be a receptacle or container arranged to receive the diamond internally to provide an imaging region, and in which the interior is substantially shut off or sealed from outside light and other interference. The integration sphere 162 may be made from plastic, metal, or any other suitable material. The inside surface of the integration sphere 162 may be coated 163 with a reflective coating to facilitate diffused reflection. The inside surface of the integration sphere 162 may be coated 163 with barium sulphate or any other suitable coating.

The inside of the integration sphere 162 may be illuminated by a light source (not shown). LED lights may be used inside the integration sphere to reduce the amount of specular reflections from the diamond. Generally, the integration sphere provides an even light distribution that is projected onto the diamond 10 when capturing images of the diamond 10. This is to avoid areas of the diamond 10 that are over-illuminated or under-illuminated that might affect the grading of the diamond 10. A white paint coating within the integration sphere 162 can be used for instance to provide an even light field. Light from the light source may be directed into the integration sphere 162 through one or more optical fibres (169 shown in FIG. 15). However, light may be introduced into the integration sphere in any suitable manner. Alternatively, a light source may be provided in the integration sphere 162 itself.

Figure 13:
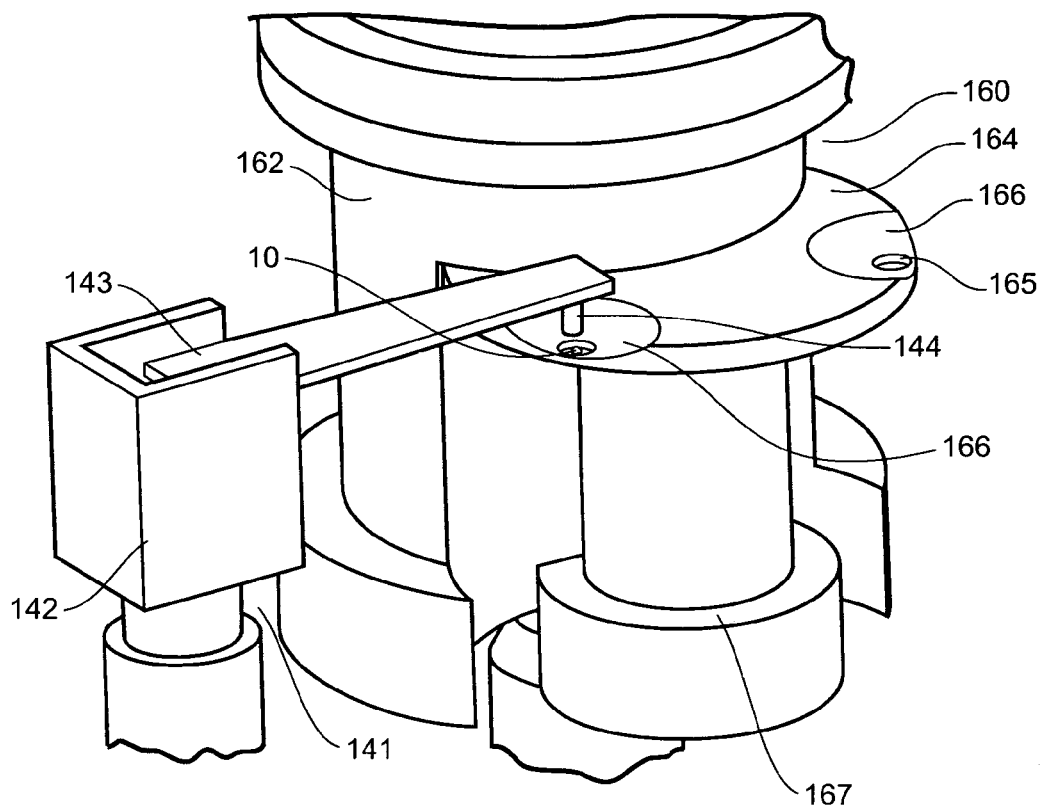
FIG. 13 is a close-up perspective view of the first robotic arm placing a diamond to be graded on a platform of the vision system of FIG. 11.
Figure 14:
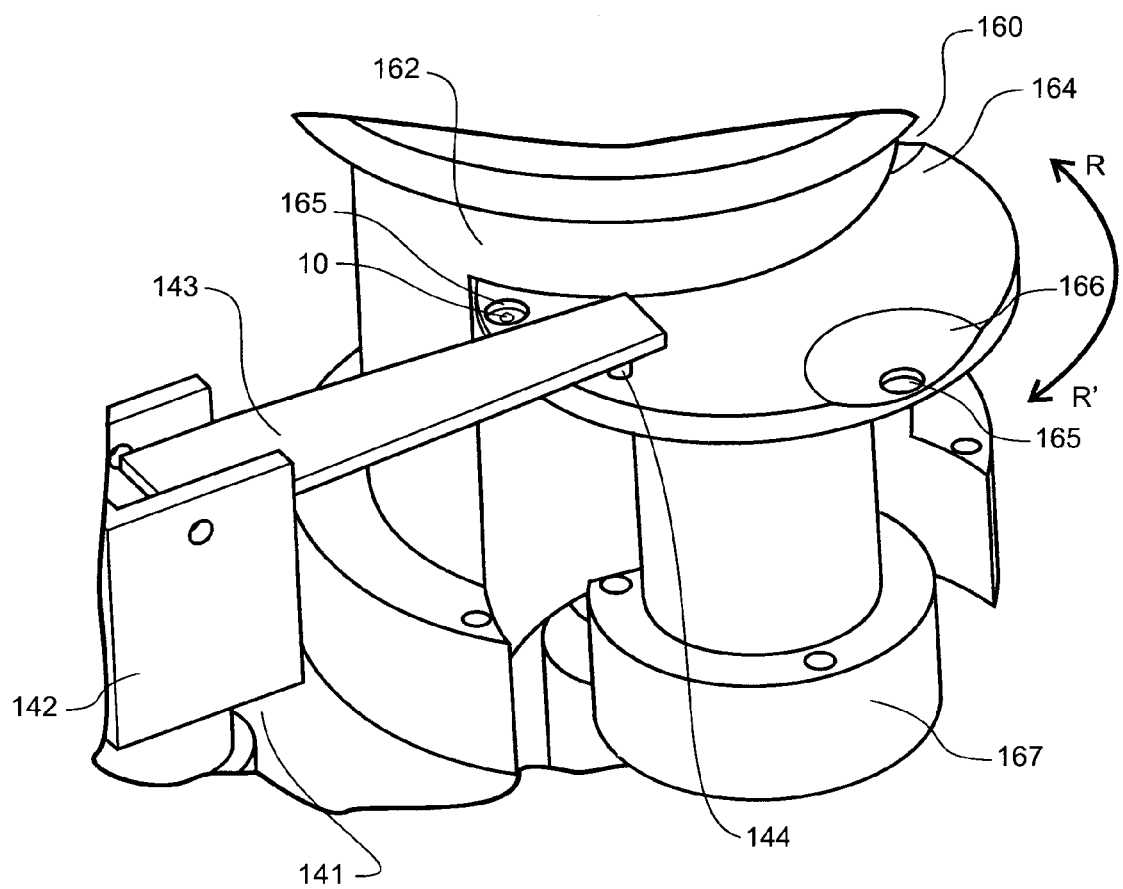
FIG. 14 is a close-up perspective view showing rotation of the platform of FIG. 13 as a diamond enters an integration sphere of the vision system.
Figure 15:
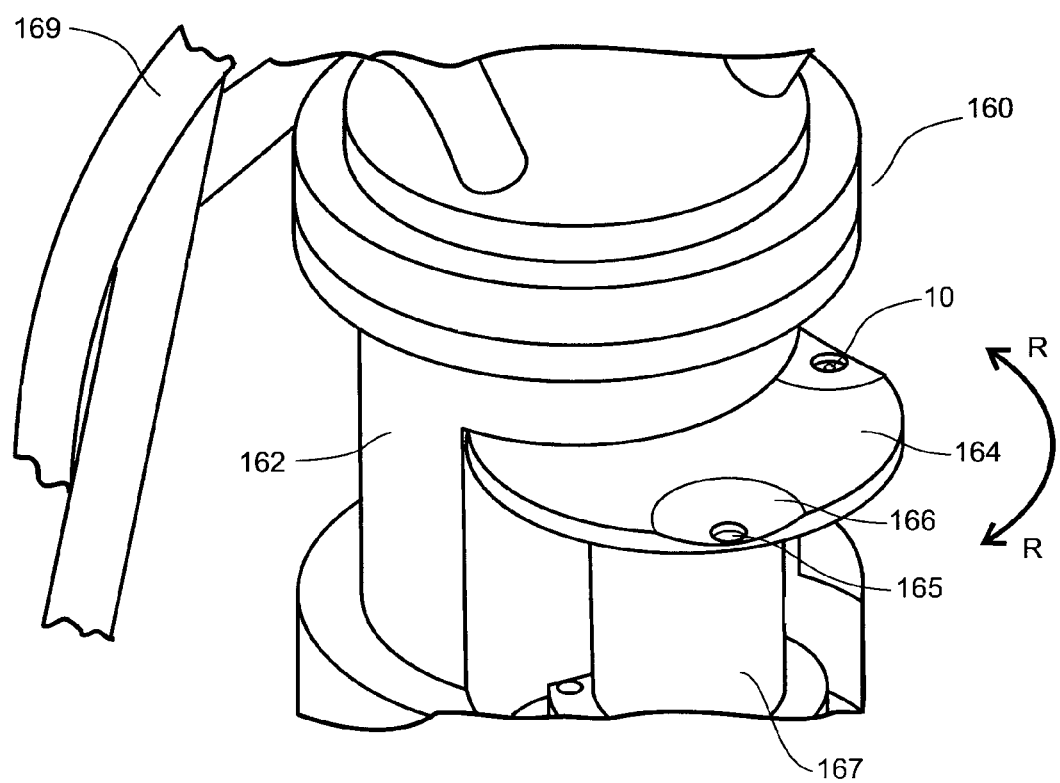
FIG. 15 is a close up perspective view showing rotation of the platform of FIG. 14 as a diamond exits the integration sphere of the vision system.

Referring to FIGS. 13 to 15, a diamond 10 may be introduced into the integration sphere 162 through a rotating platform 164 which is in the form of a disk in the preferred embodiment. As shown in FIG. 13, the diamond 10 may be placed on the rotating disk 164 by the electromechanical system 140, such as the first robotic arm 141. As discussed earlier, the arm 141 carrying the diamond 10, is arranged to release the diamond 10 from the suction head 144 and place it at the input of the vision system 160. The rotating disk 164 may then rotate (as indicated by arrow RR' in FIG. 14) and carry the diamond 10 into the integration sphere 162 for imaging. The rotating disk 164 may pass through a slit (obscured by the rotating disk 164 in the figures) in the integration sphere 162. The rotating disk may contain one or more recessed stages 165 for the diamond to sit in so that it may move through the slit without being brushed off the rotating disk 164. The rotating disk 164 may comprise three or more recessed stages 165 so that at any one time one ungraded diamond 10 may be placed at the input of the vision system 160 on the rotating disk 164 (see FIGS. 13 and 14), one diamond may be provided within the integration sphere 162, and one graded diamond 10 may be at the output of the vision system 160 ready to be removed from the rotating disk 164 (see FIG. 15). Each recessed stage 165 may comprise a further flat recess 166 for the diamond 10 to sit in. The flat recess 166 may comprise a window through the rotating disk 164 so that an image can be taken from underneath, if a camera is provided below the rotating disk 164 for example. The recessed stages 165 including the flat recesses 166 may be formed as a sapphire stage. Movement of the rotating disk 164 may by actuated by an electric motor 167 such as a stepper motor. Actuation of the rotating disk 164 may be controlled by the computer. If there are three equally spaced stages 165, then the rotating disk 164 may be arranged to rotate 120 degrees with every instruction from the computer. Once graded, the disk 164 rotates to expose the graded diamond 10, as shown in FIG. 15, ready for pick-up at the output of the vision system 160.

Figure 16:
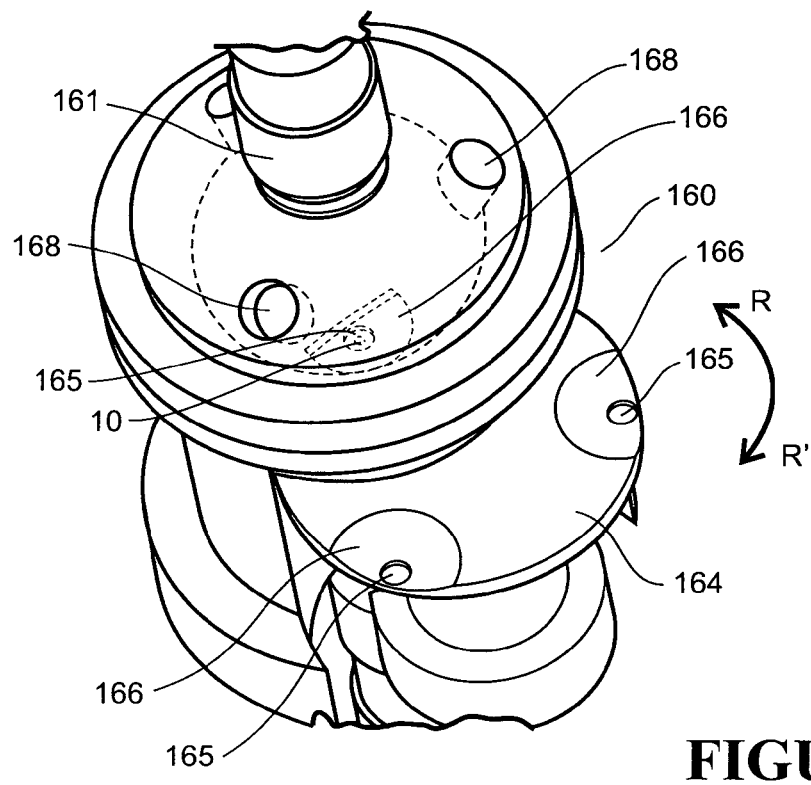
FIG. 16 is a perspective view of the vision system from the top showing a diamond within the integration sphere of the vision system.
Figure 17:
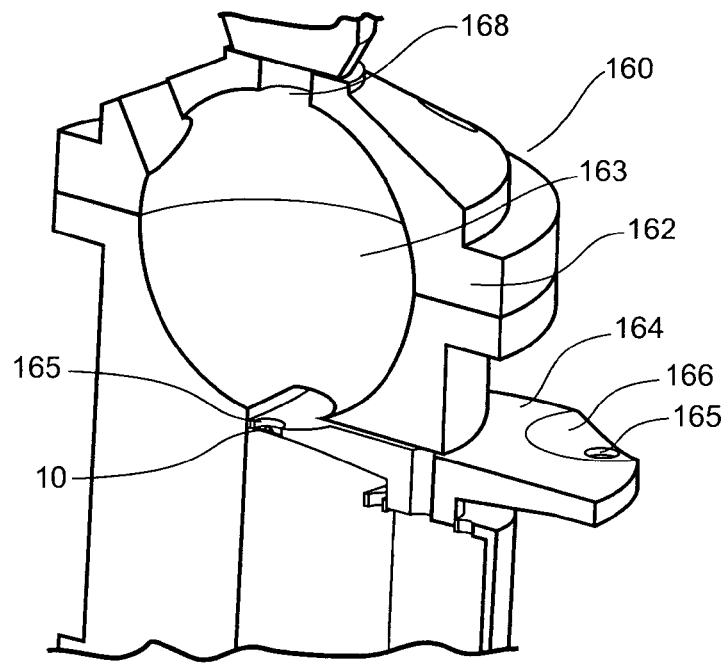
FIG. 17 is a cutaway perspective side view showing the diamond of FIG. 16 inside the integration sphere.

Referring to FIGS. 16 and 17, the inside of the integration sphere 162 may be substantially spherical in shape. The integration sphere 162 may comprise apertures 168 for the light source and camera lens 161. The rotating disk 164 may move the diamond 10 into the bottom of the integration sphere 162 for imaging of the diamond 10. Preferably the system is arranged to move the diamond into the centre position of the bottom of the integration sphere 162 to perform image capturing and acquisition. A coating 163 provided inside the inner surface of the sphere is used to facilitate diffused reflection.

The rotating disk 164 may be considered to be both the input and output from the vision system 160. For example, an oriented diamond may be placed on the rotating disk 164 by the electromechanical system 140 (in particular arm 141). The diamond 10 may then be moved inside the integration sphere 162 by the rotating disk 164 for imaging. The diamond may then be moved outside the integration sphere 162 and removed by the electromechanical system 140 (in particular arm 145).

It should be noted that any suitable system used to image the diamond 10 may be used without departing from the spirit and scope of the invention. For example, the diamond 10 may be suspended or laid on a platform for imaging and any number and type of suitable cameras may be used to image the diamond. Furthermore, the vision system 160 may be adapted to image and process/grade two or more diamonds at a time to enhance operational speed of the overall system 100.

Image Processing

Figure 18:
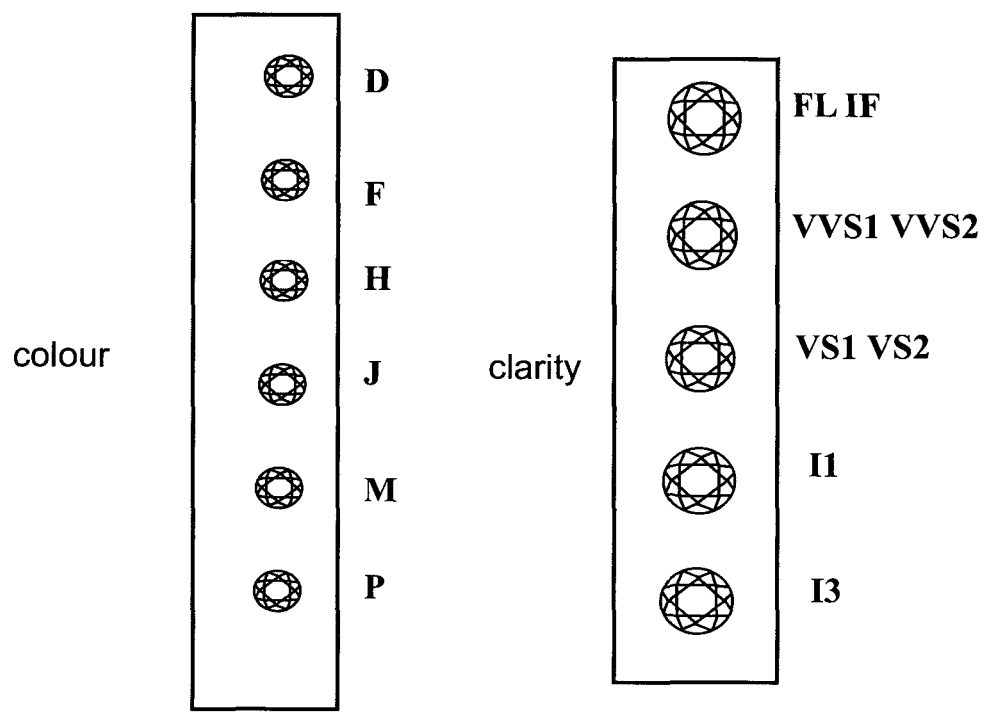
FIG. 18 shows a series of diamonds of various colour grades and clarity grades.

Referring to FIG. 18, a diamond 10 may be graded according to one or more of several characteristics, including the diamond colour and diamond clarity. For example, the Gemological Institute of America (GIA) diamond grading scale grades diamond colours from D (colourless) to Z (light yellow). Similarly, the GIA diamond clarity grading scale grades diamond clarity from FL (flawless) to $I_3$ (included). The diamond sorting system 100 may be able to grade a particular diamond's colour and clarity on a similar scale.

Once the vision system 160 has captured one or more images of a diamond, the image or data indicative of the image may be fed into a computer or processor so that an image processing algorithm can be executed to grade the diamond according to colour and clarity. In the preferred embodiment real time analysis of diamond image(s) is carried out by the processor to grade the diamond. The processor may have in memory information or a database or a look-up table indicative of a large sample of diamonds with known colour and clarity gradings. The clarity grading information or data may include information on a large sample of diamonds with known inclusions or blemishes such as clouds, feathers, knots, cleavage, polish lines, grain boundaries, nicks, pits, chips, or any other inclusion or blemish. The clarity grading or information or data may also include information as to the size of the inclusions or blemishes. A database or look-up table can be built for comparison or correlation with colour and clarity information captured from diamonds 10 in order to grade the diamonds into a specific colour or clarity grade. In the preferred embodiment only one digital image of the diamond is required for real time analysis and grading in terms of colour, and only one digital image of the diamond is required for real time analysis and grading in terms of clarity. This shortens the processing time required to grade the diamond.

Figure 19:
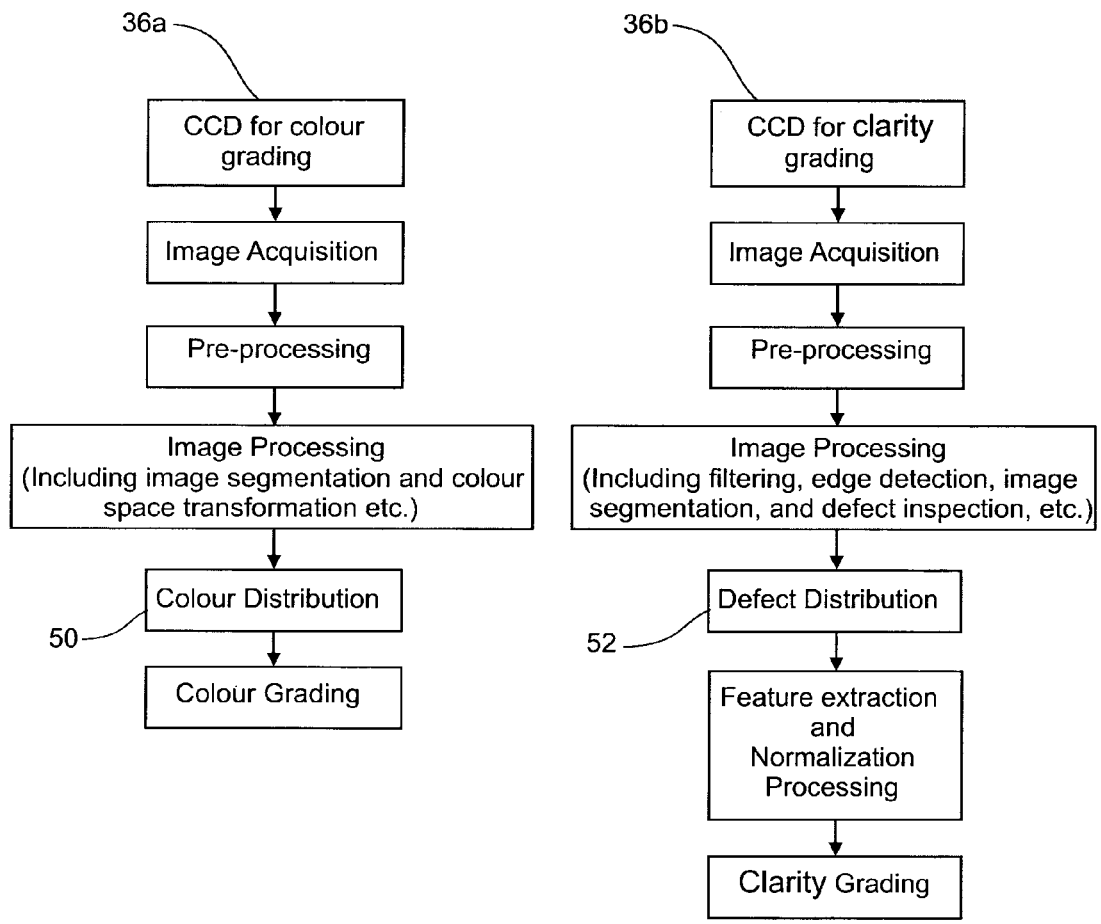
FIG. 19 is a flowchart of an algorithm for determining a colour grade and clarity grade for a diamond.

Referring to FIG. 19, a general algorithm for grading the colour and clarity of a diamond is shown. In this system the vision system 160 comprises two cameras, however in alternative embodiments any suitable number of cameras may be used. A first camera 36a may be used for colour grading and a second camera 36b may be used for clarity grading. Each camera takes an image of the diamond, and each image may then be pre-processed. Pre-processing may include extracting the image of the diamond from the background. Image processing algorithms may then be executed on each image or on data indicative of each image in order to obtain a colour and clarity grade for the diamond. Image processing techniques employed may include filtering, edge detection, image segmentation, defect inspection, fusion, or any other suitable image processing technique. For example, the edges of the diamond may be detected using edge threshold algorithms so that any data outside of the diamond is not used for determining the diamond grade. The images may be filtered to smooth out any noise. The data is then used to determine the colour grading and the clarity grading of the diamond 10. A colour grading algorithm 50 may be executed in order to determine the colour grading. Similarly, a clarity grading algorithm 52 may be executed in order to determine the clarity grading.

Figure 20:
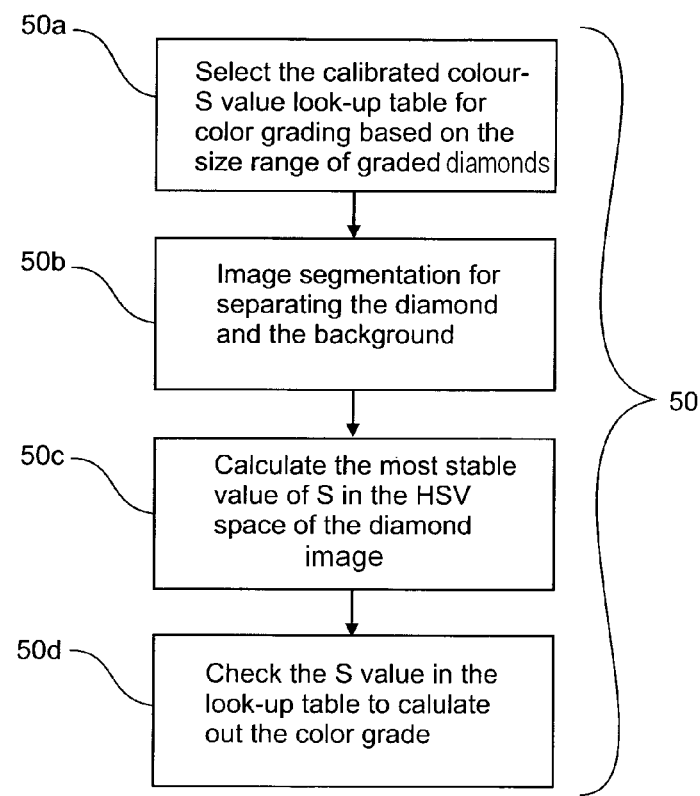
FIG. 20 is a flowchart of an algorithm for determining a colour grade for a diamond.

Referring to FIG. 20, the colour of a diamond may be evaluated by looking at the blue colour in the RGB (red-green-blue) colour space of the pre-processed image. This is due to the fact that diamonds may absorb blue light. However, there may be a minute colour variation between different colour grades of diamonds. So alternatively, the colour of a diamond may be evaluated by looking at the saturation value in the HSV (hue-saturation-value) colour space of the pre-processed image. Different sized diamonds with the same colour grading may have different saturation values so it may be necessary to select a calibrated colour-saturation value from a look-up table or database based on the size ranges of the known graded diamonds (step 50a). The image at this point or even prior may be segmented to separate the diamond and the background (step 50b). The most stable saturation value may then be calculated in the HSV space of the diamond image (step 50c). Finally, this saturation value may be compared or correlated with the information contained in the database or look-up table in order to determine the final colour grade of the diamond (step 50d).

Figure 21:
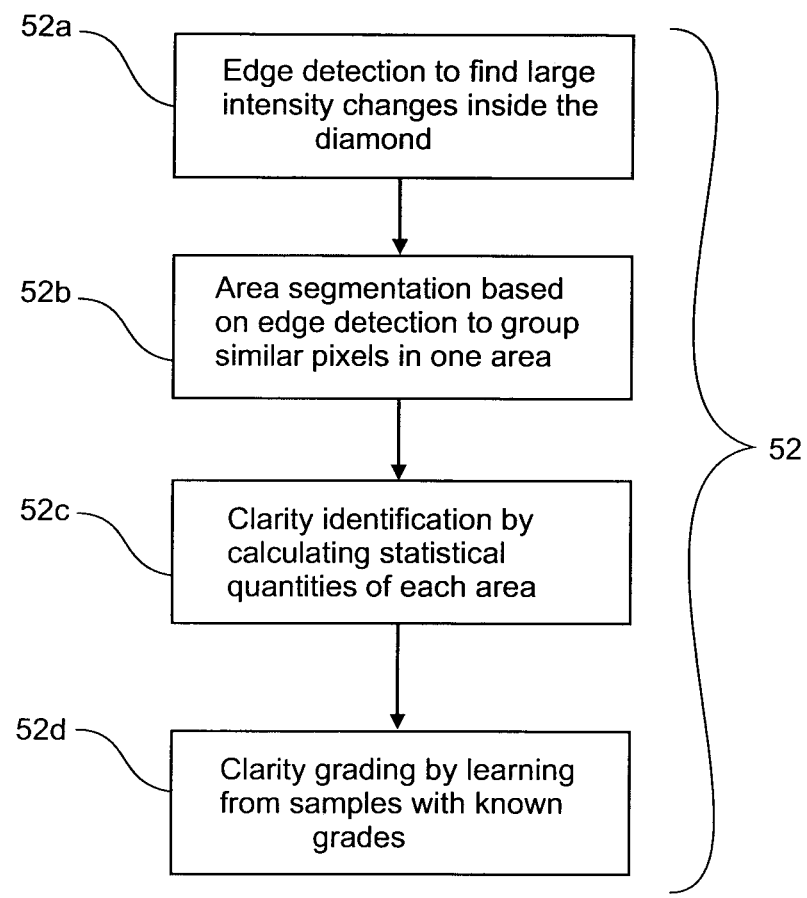
FIG. 21 is a flowchart of an algorithm for determining a clarity grade for a diamond.

Referring to FIG. 21, an edge detection algorithm may be executed on a diamond image to find large intensity changes within the diamond (step 52a). The diamond image may then be segmented into separate areas for analysis, with the detected edges acting as the boundaries in order to group nearby pixels with similar intensities (step 52b). These nearby pixels may all be indicative of one particular inclusion or blemish. Statistical quantities of the area may be extracted in order to determine whether each separated area is an inclusion or blemish or not (step 52c). The statistical quantities of each separated area may include standard deviation, entropy, uniformity, and any other suitable statistical quantity. The overall clarity grade of the diamond image may then be determined be comparing or correlating the identified inclusions with a database or look-up table of diamond samples with known clarity grades (step 52d).

The colour grading and clarity grading can then be normalised against the database of known grades in order to obtain the final colour and clarity grades.

Once the grades have been obtained, the processor or computer may control the electromechanical system 140 to deposit the diamond in the bin 183 or designated area corresponding to that particular grading.

The above image processing method is the preferred embodiment and the invention is not intended to exclude other image processing methods/algorithms for determining diamond qualities necessary for grading.

The foregoing description of the invention includes preferred forms thereof. Modifications may be made thereto without departing from the scope of the invention as defined by the accompanying claims.

What is claimed is:

1. A diamond sorting system comprising:
   a diamond source for supplying one or more diamonds to be graded,
   a vision system arranged to receive a diamond from the diamond source for grading the diamond and having:
   one or more cameras arranged to take one or more images of the diamond,
   a processor arranged to receive data indicative of the one or more images from the one or more cameras, and to execute an algorithm on the data to grade the diamond,
   a diamond collection unit arranged to receive a graded diamond from the vision system, and
   an electromechanical diamond transporter arranged to transport a diamond to be graded from the diamond source to the vision system, and further arranged to transport a graded diamond from the vision system to the diamond collection unit, and wherein the transporter comprises at least one robotic arm unit, the at least one robotic arm unit comprising a first robotic arm, moveable between the diamond source and the vision system, and configured to transport the diamond to be graded from the diamond source to the vision system for grading, and a second robotic arm, moveable between the vision system and the diamond collection unit, and configured to transport the graded diamond from the vision system to the diamond collection unit.

2. The diamond sorting system as claimed in claim 1, wherein the diamond source comprises a diamond feeder arranged to provide diamonds oriented for grading to the diamond transporter.

3. The diamond sorting system as claimed in claim 2, wherein the diamond feeder comprises a receptacle for containing therein one or more diamonds to be graded and a vibrating platform extending from said receptacle for transporting one or more diamonds onto and along the platform to a position adjacent the diamond transporter.

4. The diamond sorting system as claimed in claim 3, wherein a computer actuates vibration of the diamond feeder.

5. The diamond sorting system as claimed in claim 1, wherein the first robotic arm comprises a body part rotatable between a pick-up position adjacent to the diamond source and a drop position adjacent to the vision system.

6. The diamond sorting system as claimed in claim 5, wherein the first robotic arm further comprises an arm extending from the body part and having a suction head at a distal end thereof, the suction head being arranged to apply a suction force for picking up the diamond from the diamond source when the body part is in the pick-up position and to at least partially remove the suction force when the body part is in the drop position to release the diamond onto the vision system for grading.

7. The diamond sorting system as claimed in claim 6, wherein the arm is pivotably coupled to the body part to enable the suction head to pivot towards or away from a diamond when the body part is in the pick-up or drop position.

8. The diamond sorting system as claimed in claim 1, wherein the diamond collection unit is segmented into a plurality of segments, each segment corresponding to a particular diamond grade.

9. The diamond sorting system as claimed in claim 8, wherein the diamond collection unit comprises a segmented platform, each segment having a container for retaining a particular grade of diamond.

10. The diamond sorting system as claimed in claim 1, wherein the system comprises a computer arranged to actuate movement of the diamond transporter.

11. The diamond sorting system as claimed in claim 1, wherein the vision system is arranged to grade a diamond by colour or clarity or both.

12. The diamond sorting system as claimed in claim 1, wherein the vision system comprises at least one camera and an imaging region for retaining a diamond to be imaged by the camera and graded.

13. The diamond sorting system as claimed in claim 12, wherein the at least one camera comprises a first camera and a second camera, the first camera comprising a lens arranged to capture an image suitable for colour grading of the diamond and the second camera comprising a lens arranged to capture an image suitable for clarity grading of the diamond.

14. The diamond sorting system as claimed in claim 12, wherein the vision system comprises a light source arranged to light the diamond to be imaged.

15. The diamond sorting system as claimed in claim 1, wherein the second robotic arm comprises a first body part rotatable between a pick up position adjacent to the vision system and a drop position adjacent to the collection unit.

16. The diamond sorting system as claimed in claim 15, wherein the second robotic arm further comprises a second body part to which the first body part is rotatably coupled, the second body part being rotatable about an axis substantially parallel to and spaced from a rotation axis of the first body part.

17. The diamond sorting system as claimed in claim 1, wherein the vision system comprises an integration sphere arranged to receive a diamond and to provide an even light distribution around the diamond to be imaged.

18. The diamond sorting system as claimed in claim 17, further comprising a moveable platform for transporting the diamond into the integration sphere to be imaged and out of the integration sphere to be transported to the collection unit once graded.

19. The diamond sorting system as claimed in claim 18, wherein the platform is rotatable and passes through a slit in the integration sphere to move a diamond on the platform into and out of the integration sphere.

20. The diamond sorting system as claimed in claim 19, wherein the platform is a disk having at least one recessed stage for retaining a diamond.

21. The diamond sorting system as claimed in claim 20, wherein the disk comprises three recessed stages that are radially spaced such that during imaging one stage is within the integration sphere, one stage is adjacent to the diamond transporter for receiving a diamond from the diamond source and one stage is adjacent to the diamond transporter for providing a graded diamond to be delivered to the collection unit.

22. The diamond sorting system as claimed in claim 1, further comprising an enclosed housing for retaining the diamond source, the vision system, the diamond transporter and the diamond collection unit.

23. The diamond sorting system as claimed in claim 22, further comprising a dust ionizer in the housing for neutralising static charge within the housing.

24. A diamond sorting system comprising:
   a diamond source for supplying one or more diamonds to be graded, a vision system arranged to receive a diamond from the diamond source for grading the diamond and having:
one or more cameras arranged to take one or more images of the diamond,
a processor arranged to receive data indicative of the one or more images from the one or more cameras, and to execute an algorithm on the data to grade the diamond,
a diamond collection unit arranged to receive a graded diamond from the vision system, and
an electromechanical diamond transporter arranged to transport a diamond to be graded from the diamond source to the vision system, and further arranged to transport a graded diamond from the vision system to the diamond collection unit, and wherein the transporter comprises at least one robotic arm, each arm being moveable to transport the diamond from the source to the vision system, or from the vision system to the diamond collection unit,
wherein the diamond transporter comprises a robotic arm moveable between the vision system and the diamond collection unit for transporting a graded diamond from the vision system to the collection unit,
the robotic arm comprises a first body part rotatable between a pick up position adjacent to the vision system and a drop position adjacent to the collection unit, and
an arm extends from the first body part and comprises a suction head at a distal end thereof, the suction head being arranged to apply a suction force for picking up a diamond from the vision system when the first body part is in the pick-up position and to at least partially remove the suction force when the body part is in the drop position to release the diamond at the collection unit.

25. The diamond sorting system as claimed in claim 24, wherein the arm is pivotably coupled to the first body part to enable the suction head to pivot towards or away from a diamond when the first body part is in the pick-up or drop position.

26. An automated method of sorting one or more diamonds comprising the steps of:
transporting a diamond from a diamond source to a vision system,
taking one or more images of the diamond,
processing data indicative of the images to grade the diamond, and
transporting the diamond from the vision system to a segment of a diamond collection unit corresponding to the grade of the diamond,
wherein a first robotic arm, moveable between the diamond source and the vision system, and configured to transport the diamond from the diamond source to the vision system, performs the step of transporting the diamond from the diamond source to the vision system and a second robotic arm, moveable between the vision system and the diamond collection unit, and configured to transport the diamond from the vision system to the diamond collection unit, performs the step of transporting the diamond from the vision system to the collection unit.

27. The method as claimed in claim 26, wherein the diamond is graded by the colour of the diamond.

28. The method as claimed in claim 27, wherein the saturation value of the image of the diamond is extracted in order to grade the colour of the diamond.

29. The method as claimed in claim 26, wherein the diamond is graded by the clarity of the diamond.

30. The method as claimed in claim 29, wherein large intensity changes in the image of the diamond are identified in order to grade the clarity of the diamond.

* * * * *